United States Patent
Jasmin et al.

(10) Patent No.: US 12,201,671 B2
(45) Date of Patent: Jan. 21, 2025

(54) POLYPEPTIDES FOR TREATMENT OF CANCER

(71) Applicant: Saint Joseph's University, Philadelphia, PA (US)

(72) Inventors: Jean-Francois Jasmin, Philadelphia, PA (US); Shannon Chilewski, Philadelphia, PA (US); Isabelle Mercier, Philadelphia, PA (US)

(73) Assignee: Saint Joseph's University, Philadelphia, PA (US)

( * ) Notice: Subject to any disclaimer, the term of this patent is extended or adjusted under 35 U.S.C. 154(b) by 509 days.

(21) Appl. No.: 17/607,100

(22) PCT Filed: May 13, 2020

(86) PCT No.: PCT/US2020/032638
§ 371 (c)(1),
(2) Date: Oct. 28, 2021

(87) PCT Pub. No.: WO2020/232095
PCT Pub. Date: Nov. 19, 2020

(65) Prior Publication Data
US 2022/0184177 A1 Jun. 16, 2022

Related U.S. Application Data

(60) Provisional application No. 62/848,980, filed on May 16, 2019.

(51) Int. Cl.
*A61K 38/17* (2006.01)
*A61K 45/06* (2006.01)
*A61P 35/00* (2006.01)

(52) U.S. Cl.
CPC .......... *A61K 38/1709* (2013.01); *A61K 45/06* (2013.01); *A61P 35/00* (2018.01)

(58) Field of Classification Search
CPC ...... A61K 38/1709; A61K 45/06; A61P 35/00
See application file for complete search history.

(56) References Cited

U.S. PATENT DOCUMENTS

| | | | | |
|---|---|---|---|---|
| 7,608,413 B1 * | 10/2009 | Joseloff | ............ | G01N 33/57484 424/178.1 |
| 7,745,391 B2 * | 6/2010 | Mintz | ............ | A61P 37/00 514/19.3 |
| 7,842,467 B1 * | 11/2010 | Heidbrink | ............ | A61P 35/00 435/7.1 |
| 8,685,652 B2 * | 4/2014 | Friebe | ............ | A61P 31/18 435/7.1 |
| 9,597,380 B2 * | 3/2017 | Chakraborty | ............ | C12N 15/67 |
| 11,446,398 B2 * | 9/2022 | Barrett | ............ | C07K 14/5428 |
| 2001/0008758 A1 | 7/2001 | McHale et al. | | |
| 2003/0109690 A1 * | 6/2003 | Ruben | ............ | C07K 14/47 536/23.1 |
| 2007/0026409 A1 * | 2/2007 | Woolf | ............ | C12Q 1/6883 435/6.16 |
| 2007/0061916 A1 * | 3/2007 | Kovalic | ............ | C07K 14/415 536/23.6 |
| 2010/0239581 A1 * | 9/2010 | Joseloff | ............ | A61P 13/12 436/501 |
| 2011/0093962 A1 * | 4/2011 | Heidbrink | ............ | A61P 35/00 435/235.1 |
| 2017/0349628 A1 | 12/2017 | Suh et al. | | |

OTHER PUBLICATIONS

Campbell, et al., "CAPER as a therapeutic target for triple negative breast cancer", Oncotarget, vol. 9, No. 54, Jul. 13, 2018, pp. 30340-30354.
Chai, et al., "Overexpression of HCC1/CAPERα may play a role in lung cancer carcinogenesis", Tumour Biol, vol. 35, No. 7, Jul. 2014, pp. 6311-6317.
Jung, et al., "Molecular Cloning and Characterization of CAPER, a Novel Coactivator of Activating Protein-1 and Estrogen Receptors", J Biol Chem, vol. 277, No. 2, 2002, pp. 1229-1234.
Mercier, et al., "CAPER, a novel regulator of human breast cancer progression", Cell Cycle, vol. 13, No. 8, Feb. 17, 2014, pp. 1256-1264.
Pimiento, et al., "Knockdown of CSE1L Gene in Colorectal Cancer Reduces Tumorigenesis in Vitro", Am J Pathol, vol. 186, No. 10, Oct. 2016, pp. 2761-2768.
Sillars-Hardebol, et al., "CSE1L, DID01 and RBM39 in colorectal adenoma to carcinoma progression", Cell Oncol, vol. 35, No. 4, 2012, pp. 293-300.
International Search Report & Written Opinion dated Oct. 23, 2020 for corresponding PCT International Application No. PCT/US2020/032638.
Chilewski, et al., "Development of CAPER peptides for the treatment of triple negative breast cancer", Cell Cycle, vol. 19, No. 4, 2020, pp. 432-447.
European Search Report dated Dec. 21, 2022 for corresponding European Application 20 804 866.0.

* cited by examiner

*Primary Examiner* — Amber D Steele
(74) *Attorney, Agent, or Firm* — Saul Ewing LLP; Domingos J. Silva; Chihao Wang

(57) ABSTRACT

The present-disclosure provides methods of treating cancer with certain co-activator of activator protein-1 and estrogen receptor (CAPER)-based polypeptides. In certain embodiments, the methods of the-disclosure target only cancerous cells without adversely affecting non-cancerous cells.

14 Claims, 27 Drawing Sheets
Specification includes a Sequence Listing.

SEQUENCE LISTING

```
<160> NUMBER OF SEQ ID NOS: 50

<210> SEQ ID NO 1
<211> LENGTH: 45
<212> TYPE: PRT
<213> ORGANISM: Artificial Sequence
<220> FEATURE:
<223> OTHER INFORMATION: Chemically synthesized

<400> SEQUENCE: 1

Arg Leu Gln Leu Met Ala Arg Leu Ala Glu Gly Thr Gly Leu Gln Ile
1               5                   10                  15

Pro Pro Ala Ala Gln Gln Ala Leu Gln Met Ser Gly Ser Leu Ala Phe
            20                  25                  30

Gly Ala Val Ala Asp Leu Gln Thr Arg Leu Ser Gln Gln
        35                  40                  45

<210> SEQ ID NO 2
<211> LENGTH: 45
<212> TYPE: PRT
<213> ORGANISM: Artificial Sequence
<220> FEATURE:
```

<223> OTHER INFORMATION: Chemically synthesized

<400> SEQUENCE: 2

Arg Leu Gln Leu Met Ala Arg Leu Ala Glu Gly Thr Gly Leu Gln Ile
1               5                   10                  15

Pro Pro Ala Ala Gln Gln Ala Leu Gln Met Ser Gly Ser Leu Ala Phe
            20                  25                  30

Gly Ala Val Ala Glu Phe Ser Phe Val Ile Asp Leu Gln
        35                  40                  45

<210> SEQ ID NO 3
<211> LENGTH: 45
<212> TYPE: PRT
<213> ORGANISM: Artificial Sequence
<220> FEATURE:
<223> OTHER INFORMATION: Chemically synthesized

<400> SEQUENCE: 3

Val Gly Asp Ala Leu Gln Gly Leu Arg Leu Phe Ser Thr Gln Ala Ser
1               5                   10                  15

Ile Gly Ala Gln Met Glu Gln Leu Ala Ala Gln Pro Leu Arg Ala Gly
            20                  25                  30

Gln Met Leu Gln Leu Ala Gln Ala Ser Pro Leu Arg Thr
        35                  40                  45

<210> SEQ ID NO 4
<211> LENGTH: 11
<212> TYPE: PRT
<213> ORGANISM: Artificial Sequence
<220> FEATURE:
<223> OTHER INFORMATION: Chemically synthesized

<400> SEQUENCE: 4

Tyr Gly Arg Lys Lys Arg Arg Gln Arg Arg
1               5                   10

<210> SEQ ID NO 5
<211> LENGTH: 56
<212> TYPE: PRT
<213> ORGANISM: Artificial Sequence
<220> FEATURE:
<223> OTHER INFORMATION: Chemically synthesized

<400> SEQUENCE: 5

Tyr Gly Arg Lys Lys Arg Arg Gln Arg Arg Arg Leu Gln Leu Met
1               5                   10                  15

Ala Arg Leu Ala Glu Gly Thr Gly Leu Gln Ile Pro Pro Ala Ala Gln
            20                  25                  30

Gln Ala Leu Gln Met Ser Gly Ser Leu Ala Phe Gly Ala Val Ala Asp
        35                  40                  45

Leu Gln Thr Arg Leu Ser Gln Gln
    50                  55

<210> SEQ ID NO 6
<211> LENGTH: 56
<212> TYPE: PRT
<213> ORGANISM: Artificial Sequence
<220> FEATURE:
<223> OTHER INFORMATION: Chemically synthesized

<400> SEQUENCE: 6

Tyr Gly Arg Lys Lys Arg Arg Gln Arg Arg Arg Leu Gln Leu Met
1               5                   10                  15

```
Ala Arg Leu Ala Glu Gly Thr Gly Leu Gln Ile Pro Pro Ala Ala Gln
            20                  25                  30

Gln Ala Leu Gln Met Ser Gly Ser Leu Ala Phe Gly Ala Val Ala Glu
            35                  40                  45

Phe Ser Phe Val Ile Asp Leu Gln
        50                  55

<210> SEQ ID NO 7
<211> LENGTH: 56
<212> TYPE: PRT
<213> ORGANISM: Artificial Sequence
<220> FEATURE:
<223> OTHER INFORMATION: Chemically synthesized

<400> SEQUENCE: 7

Tyr Gly Arg Lys Lys Arg Arg Gln Arg Arg Val Gly Asp Ala Leu
1               5                   10                  15

Gln Gly Leu Arg Leu Phe Ser Thr Gln Ala Ser Ile Gly Ala Gln Met
            20                  25                  30

Glu Gln Leu Ala Ala Gln Pro Leu Arg Ala Gly Gln Met Leu Gln Leu
            35                  40                  45

Ala Gln Ala Ser Pro Leu Arg Thr
        50                  55

<210> SEQ ID NO 8
<211> LENGTH: 524
<212> TYPE: PRT
<213> ORGANISM: Artificial Sequence
<220> FEATURE:
<223> OTHER INFORMATION: Chemically synthesized

<400> SEQUENCE: 8

Met Ala Asp Asp Ile Asp Ile Glu Ala Met Leu Glu Ala Pro Tyr Lys
1               5                   10                  15

Lys Asp Glu Asn Lys Leu Ser Ser Ala Asn Gly His Glu Glu Arg Ser
            20                  25                  30

Lys Lys Arg Lys Lys Ser Lys Ser Arg Ser Arg Ser His Glu Arg Lys
            35                  40                  45

Arg Ser Lys Ser Lys Glu Arg Lys Arg Ser Arg Asp Arg Glu Arg Lys
        50                  55                  60

Lys Ser Lys Ser Arg Glu Arg Lys Arg Ser Arg Ser Lys Glu Arg Arg
65                  70                  75                  80

Arg Ser Arg Ser Arg Ser Arg Asp Arg Arg Phe Arg Gly Arg Tyr Arg
                85                  90                  95

Ser Pro Tyr Ser Gly Pro Lys Phe Asn Ser Ala Ile Arg Gly Lys Ile
                100                 105                 110

Gly Leu Pro His Ser Ile Lys Leu Ser Arg Arg Arg Ser Arg Ser Lys
            115                 120                 125

Ser Pro Phe Arg Lys Asp Lys Ser Pro Val Arg Glu Pro Ile Asp Asn
        130                 135                 140

Leu Thr Pro Glu Glu Arg Asp Ala Arg Thr Val Phe Cys Met Gln Leu
145                 150                 155                 160

Ala Ala Arg Ile Arg Pro Arg Asp Leu Glu Glu Phe Phe Ser Thr Val
                165                 170                 175

Gly Lys Val Arg Asp Val Arg Met Ile Ser Asp Arg Asn Ser Arg Arg
                180                 185                 190
```

Ser Lys Gly Ile Ala Tyr Val Glu Phe Val Asp Val Ser Ser Val Pro
    195                 200                 205

Leu Ala Ile Gly Leu Thr Gly Gln Arg Val Leu Gly Val Pro Ile Ile
210                 215                 220

Val Gln Ala Ser Gln Ala Glu Lys Asn Arg Ala Ala Met Ala Asn
225                 230                 235                 240

Asn Leu Gln Lys Gly Ser Ala Gly Pro Met Arg Leu Tyr Val Gly Ser
                245                 250                 255

Leu His Phe Asn Ile Thr Glu Asp Met Leu Arg Gly Ile Phe Glu Pro
            260                 265                 270

Phe Gly Arg Ile Glu Ser Ile Gln Leu Met Met Asp Ser Glu Thr Gly
        275                 280                 285

Arg Ser Lys Gly Tyr Gly Phe Ile Thr Phe Ser Asp Ser Glu Cys Ala
    290                 295                 300

Lys Lys Ala Leu Glu Gln Leu Asn Gly Phe Glu Leu Ala Gly Arg Pro
305                 310                 315                 320

Met Lys Val Gly His Val Thr Glu Arg Thr Asp Ala Ser Ser Ala Ser
                325                 330                 335

Ser Phe Leu Asp Ser Asp Glu Leu Glu Arg Thr Gly Ile Asp Leu Gly
            340                 345                 350

Thr Thr Gly Arg Leu Gln Leu Met Ala Arg Leu Ala Glu Gly Thr Gly
        355                 360                 365

Leu Gln Ile Pro Pro Ala Ala Gln Ala Leu Gln Met Ser Gly Ser
    370                 375                 380

Leu Ala Phe Gly Ala Val Ala Asp Leu Gln Thr Arg Leu Ser Gln Gln
385                 390                 395                 400

Thr Glu Ala Ser Ala Leu Ala Ala Ala Ser Val Gln Pro Leu Ala
                405                 410                 415

Thr Gln Cys Phe Gln Leu Ser Asn Met Phe Asn Pro Gln Thr Glu Glu
            420                 425                 430

Glu Val Gly Trp Asp Thr Glu Ile Lys Asp Asp Val Ile Glu Glu Cys
        435                 440                 445

Asn Lys His Gly Gly Val Ile His Ile Tyr Val Asp Lys Asn Ser Ala
    450                 455                 460

Gln Gly Asn Val Tyr Val Lys Cys Pro Ser Ile Ala Ala Ala Ile Ala
465                 470                 475                 480

Ala Val Asn Ala Leu His Gly Arg Trp Phe Ala Gly Lys Met Ile Thr
                485                 490                 495

Ala Ala Tyr Val Pro Leu Pro Thr Tyr His Asn Leu Phe Pro Asp Ser
            500                 505                 510

Met Thr Ala Thr Gln Leu Leu Val Pro Ser Arg Arg
        515                 520

<210> SEQ ID NO 9
<211> LENGTH: 530
<212> TYPE: PRT
<213> ORGANISM: Artificial Sequence
<220> FEATURE:
<223> OTHER INFORMATION: Chemically synthesized

<400> SEQUENCE: 9

Met Ala Asp Asp Ile Asp Ile Glu Ala Met Leu Glu Ala Pro Tyr Lys
1               5                   10                  15

Lys Asp Glu Asn Lys Leu Ser Ser Ala Asn Gly His Glu Glu Arg Ser
            20                  25                  30

```
Lys Lys Arg Lys Lys Ser Lys Ser Arg Ser Arg Ser His Glu Arg Lys
            35                  40                  45

Arg Ser Lys Ser Lys Glu Arg Lys Arg Ser Arg Asp Arg Glu Arg Lys
     50                  55                  60

Lys Ser Lys Ser Arg Glu Arg Lys Arg Ser Arg Ser Lys Glu Arg Arg
65                  70                  75                  80

Arg Ser Arg Ser Arg Ser Arg Asp Arg Phe Arg Gly Arg Tyr Arg
             85                  90                  95

Ser Pro Tyr Ser Gly Pro Lys Phe Asn Ser Ala Ile Arg Gly Lys Ile
             100                 105                 110

Gly Leu Pro His Ser Ile Lys Leu Ser Arg Arg Ser Arg Ser Lys
             115                 120                 125

Ser Pro Phe Arg Lys Asp Lys Ser Pro Val Arg Glu Pro Ile Asp Asn
             130                 135                 140

Leu Thr Pro Glu Glu Arg Asp Ala Arg Thr Val Phe Cys Met Gln Leu
145                 150                 155                 160

Ala Ala Arg Ile Arg Pro Arg Asp Leu Glu Glu Phe Phe Ser Thr Val
                 165                 170                 175

Gly Lys Val Arg Asp Val Arg Met Ile Ser Asp Arg Asn Ser Arg Arg
             180                 185                 190

Ser Lys Gly Ile Ala Tyr Val Glu Phe Val Asp Val Ser Ser Val Pro
         195                 200                 205

Leu Ala Ile Gly Leu Thr Gly Gln Arg Val Leu Gly Val Pro Ile Ile
             210                 215                 220

Val Gln Ala Ser Gln Ala Glu Lys Asn Arg Ala Ala Met Ala Asn
225                 230                 235                 240

Asn Leu Gln Lys Gly Ser Ala Gly Pro Met Arg Leu Tyr Val Gly Ser
                 245                 250                 255

Leu His Phe Asn Ile Thr Glu Asp Met Leu Arg Gly Ile Phe Glu Pro
             260                 265                 270

Phe Gly Arg Ile Glu Ser Ile Gln Leu Met Met Asp Ser Glu Thr Gly
         275                 280                 285

Arg Ser Lys Gly Tyr Gly Phe Ile Thr Phe Ser Asp Ser Glu Cys Ala
     290                 295                 300

Lys Lys Ala Leu Glu Gln Leu Asn Gly Phe Glu Leu Ala Gly Arg Pro
305                 310                 315                 320

Met Lys Val Gly His Val Thr Glu Arg Thr Asp Ala Ser Ser Ala Ser
             325                 330                 335

Ser Phe Leu Asp Ser Asp Glu Leu Glu Arg Thr Gly Ile Asp Leu Gly
             340                 345                 350

Thr Thr Gly Arg Leu Gln Leu Met Ala Arg Leu Ala Glu Gly Thr Gly
             355                 360                 365

Leu Gln Ile Pro Pro Ala Ala Gln Gln Ala Leu Gln Met Ser Gly Ser
     370                 375                 380

Leu Ala Phe Gly Ala Val Ala Glu Phe Ser Phe Val Ile Asp Leu Gln
385                 390                 395                 400

Thr Arg Leu Ser Gln Gln Thr Glu Ala Ser Ala Leu Ala Ala Ala
                 405                 410                 415

Ser Val Gln Pro Leu Ala Thr Gln Cys Phe Gln Leu Ser Asn Met Phe
             420                 425                 430

Asn Pro Gln Thr Glu Glu Val Gly Trp Asp Thr Glu Ile Lys Asp
             435                 440                 445
```

```
Asp Val Ile Glu Glu Cys Asn Lys His Gly Gly Val Ile His Ile Tyr
    450                 455                 460

Val Asp Lys Asn Ser Ala Gln Gly Asn Val Tyr Val Lys Cys Pro Ser
465                 470                 475                 480

Ile Ala Ala Ala Ile Ala Ala Val Asn Ala Leu His Gly Arg Trp Phe
                485                 490                 495

Ala Gly Lys Met Ile Thr Ala Ala Tyr Val Pro Leu Pro Thr Tyr His
                500                 505                 510

Asn Leu Phe Pro Asp Ser Met Thr Ala Thr Gln Leu Leu Val Pro Ser
        515                 520                 525

Arg Arg
    530

<210> SEQ ID NO 10
<211> LENGTH: 16
<212> TYPE: PRT
<213> ORGANISM: Artificial Sequence
<220> FEATURE:
<223> OTHER INFORMATION: Chemically synthesized

<400> SEQUENCE: 10

Arg Gln Ile Lys Ile Trp Phe Gln Asn Arg Arg Met Lys Trp Lys Lys
1               5                   10                  15

<210> SEQ ID NO 11
<211> LENGTH: 10
<212> TYPE: PRT
<213> ORGANISM: Artificial Sequence
<220> FEATURE:
<223> OTHER INFORMATION: Chemically synthesized

<400> SEQUENCE: 11

Pro Arg Pro Leu Pro Phe Pro Arg Pro Gly
1               5                   10

<210> SEQ ID NO 12
<211> LENGTH: 19
<212> TYPE: PRT
<213> ORGANISM: Artificial Sequence
<220> FEATURE:
<223> OTHER INFORMATION: Chemically synthesized

<400> SEQUENCE: 12

Lys Met Thr Arg Ala Gln Arg Arg Ala Ala Ala Arg Arg Asn Arg Trp
1               5                   10                  15

Thr Ala Arg

<210> SEQ ID NO 13
<211> LENGTH: 21
<212> TYPE: PRT
<213> ORGANISM: Artificial Sequence
<220> FEATURE:
<223> OTHER INFORMATION: Chemically synthesized

<400> SEQUENCE: 13

Thr Arg Ser Ser Arg Ala Gly Leu Gln Phe Pro Val Gly Arg Val His
1               5                   10                  15

Arg Leu Leu Arg Lys
            20

<210> SEQ ID NO 14
<211> LENGTH: 20
<212> TYPE: PRT
```

```
<213> ORGANISM: Artificial Sequence
<220> FEATURE:
<223> OTHER INFORMATION: Chemically synthesized

<400> SEQUENCE: 14

Gly Leu Trp Arg Ala Leu Trp Arg Leu Leu Arg Ser Leu Trp Arg Leu
1               5                   10                  15

Leu Trp Arg Ala
            20

<210> SEQ ID NO 15
<211> LENGTH: 20
<212> TYPE: PRT
<213> ORGANISM: Artificial Sequence
<220> FEATURE:
<223> OTHER INFORMATION: Chemically synthesized

<400> SEQUENCE: 15

Lys Leu Arg Thr Arg Ala Gln Arg Arg Ala Ala Ala Arg Lys Asn Lys
1               5                   10                  15

Arg Asn Thr Arg
            20

<210> SEQ ID NO 16
<211> LENGTH: 29
<212> TYPE: PRT
<213> ORGANISM: Artificial Sequence
<220> FEATURE:
<223> OTHER INFORMATION: Chemically synthesized
<220> FEATURE:
<221> NAME/KEY: MOD_RES
<222> LOCATION: (1)..(9)
<223> OTHER INFORMATION: D-enantiomers

<400> SEQUENCE: 16

Arg Arg Arg Arg Arg Arg Arg Arg Arg Lys Phe Val Arg Arg Ser Arg
1               5                   10                  15

Arg Pro Arg Thr Ala Ser Cys Ala Leu Ala Phe Val Asn
            20                  25

<210> SEQ ID NO 17
<211> LENGTH: 9
<212> TYPE: PRT
<213> ORGANISM: Artificial Sequence
<220> FEATURE:
<223> OTHER INFORMATION: Chemically synthesized
<220> FEATURE:
<221> NAME/KEY: MOD_RES
<222> LOCATION: (1)..(9)
<223> OTHER INFORMATION: D-enantiomers

<400> SEQUENCE: 17

Arg Arg Arg Gln Arg Arg Lys Lys Arg
1               5

<210> SEQ ID NO 18
<211> LENGTH: 15
<212> TYPE: PRT
<213> ORGANISM: Artificial Sequence
<220> FEATURE:
<223> OTHER INFORMATION: Chemically synthesized

<400> SEQUENCE: 18

Arg Arg Arg Arg Asn Arg Thr Arg Arg Asn Arg Arg Val Arg
1               5                   10                  15
```

```
<210> SEQ ID NO 19
<211> LENGTH: 24
<212> TYPE: PRT
<213> ORGANISM: Artificial Sequence
<220> FEATURE:
<223> OTHER INFORMATION: Chemically synthesized

<400> SEQUENCE: 19

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 20
<211> LENGTH: 17
<212> TYPE: PRT
<213> ORGANISM: Artificial Sequence
<220> FEATURE:
<223> OTHER INFORMATION: Chemically synthesized

<400> SEQUENCE: 20

Thr Arg Gln Ala Arg Arg Asn Arg Arg Arg Trp Arg Glu Arg Gln
1               5                   10                  15

Arg

<210> SEQ ID NO 21
<211> LENGTH: 12
<212> TYPE: PRT
<213> ORGANISM: Artificial Sequence
<220> FEATURE:
<223> OTHER INFORMATION: Chemically synthesized

<400> SEQUENCE: 21

Thr Ser Pro Leu Asn Ile His Asn Gly Gln Lys Leu
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Chemically synthesized

<400> SEQUENCE: 22

Thr Arg Arg Gln Arg Thr Arg Arg Ala Arg Arg Asn Arg
1               5                   10

<210> SEQ ID NO 23
<211> LENGTH: 16
<212> TYPE: PRT
<213> ORGANISM: Artificial Sequence
<220> FEATURE:
<223> OTHER INFORMATION: Chemically synthesized

<400> SEQUENCE: 23

Ala Ala Val Ala Leu Leu Pro Ala Val Leu Leu Ala Leu Leu Ala Pro
1               5                   10                  15

<210> SEQ ID NO 24
<211> LENGTH: 10
<212> TYPE: PRT
<213> ORGANISM: Artificial Sequence
<220> FEATURE:
<223> OTHER INFORMATION: Chemically synthesized
```

-continued

```
<400> SEQUENCE: 24

Val Pro Met Leu Lys Pro Met Leu Lys Glu
1               5                   10

<210> SEQ ID NO 25
<211> LENGTH: 36
<212> TYPE: PRT
<213> ORGANISM: Artificial Sequence
<220> FEATURE:
<223> OTHER INFORMATION: Chemically synthesized

<400> SEQUENCE: 25

Lys Leu Ala Leu Lys Leu Ala Leu His Ala Leu Lys Ala Ala Leu Lys
1               5                   10                  15

Leu Ala Lys Leu Ala Leu Lys Leu Ala Leu Lys Ala Leu Lys Ala Ala
            20                  25                  30

Leu Lys Leu Ala
        35

<210> SEQ ID NO 26
<211> LENGTH: 27
<212> TYPE: PRT
<213> ORGANISM: Artificial Sequence
<220> FEATURE:
<223> OTHER INFORMATION: Chemically synthesized

<400> SEQUENCE: 26

Gly Ala Leu Phe Leu Ala Phe Leu Ala Ala Ala Leu Ser Leu Met Gly
1               5                   10                  15

Leu Trp Ser Gln Pro Lys Lys Lys Arg Arg Val
            20                  25

<210> SEQ ID NO 27
<211> LENGTH: 27
<212> TYPE: PRT
<213> ORGANISM: Artificial Sequence
<220> FEATURE:
<223> OTHER INFORMATION: Chmeically synthesized

<400> SEQUENCE: 27

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 28
<211> LENGTH: 17
<212> TYPE: PRT
<213> ORGANISM: Artificial Sequence
<220> FEATURE:
<223> OTHER INFORMATION: Chemically synthesized

<400> SEQUENCE: 28

Asn Ala Lys Thr Arg Arg His Glu Arg Arg Arg Lys Leu Ala Ile Glu
1               5                   10                  15

Arg

<210> SEQ ID NO 29
<211> LENGTH: 16
<212> TYPE: PRT
<213> ORGANISM: Artificial Sequence
<220> FEATURE:
<223> OTHER INFORMATION: Chemically synthesized
```

<400> SEQUENCE: 29

Arg Gln Ile Lys Ile Phe Phe Gln Asn Arg Arg Met Lys Phe Lys Lys
1               5                   10                  15

<210> SEQ ID NO 30
<211> LENGTH: 21
<212> TYPE: PRT
<213> ORGANISM: Artificial Sequence
<220> FEATURE:
<223> OTHER INFORMATION: Chemically synthesized

<400> SEQUENCE: 30

Lys Glu Thr Trp Trp Glu Thr Trp Trp Thr Glu Trp Ser Gln Pro Lys
1               5                   10                  15

Lys Lys Arg Arg Val
            20

<210> SEQ ID NO 31
<211> LENGTH: 15
<212> TYPE: PRT
<213> ORGANISM: Artificial Sequence
<220> FEATURE:
<223> OTHER INFORMATION: Chemically synthesized

<400> SEQUENCE: 31

Ser Asp Leu Trp Glu Met Met Met Val Ser Leu Ala Cys Gln Tyr
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Chemically synthesized

<400> SEQUENCE: 32

Arg Val Ile Arg Val Trp Phe Gln Asn Lys Arg Cys Lys Asp Lys Lys
1               5                   10                  15

<210> SEQ ID NO 33
<211> LENGTH: 18
<212> TYPE: PRT
<213> ORGANISM: Artificial Sequence
<220> FEATURE:
<223> OTHER INFORMATION: Chemically synthesized

<400> SEQUENCE: 33

Leu Leu Ile Ile Leu Arg Arg Arg Ile Arg Lys Gln Ala His Ala His
1               5                   10                  15

Ser Lys

<210> SEQ ID NO 34
<211> LENGTH: 8
<212> TYPE: PRT
<213> ORGANISM: Artificial Sequence
<220> FEATURE:
<223> OTHER INFORMATION: Chemically synthesized

<400> SEQUENCE: 34

Arg Arg Arg Arg Arg Arg Arg Trp
1               5

<210> SEQ ID NO 35
<211> LENGTH: 41

```
<212> TYPE: PRT
<213> ORGANISM: Artificial Sequence
<220> FEATURE:
<223> OTHER INFORMATION: Chemically synthesized

<400> SEQUENCE: 35

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly Gly Gly Gly
            20                  25                  30

Arg Arg Arg Arg Arg Arg Arg Arg Arg
        35                  40

<210> SEQ ID NO 36
<211> LENGTH: 18
<212> TYPE: PRT
<213> ORGANISM: Artificial Sequence
<220> FEATURE:
<223> OTHER INFORMATION: Chemically synthesized

<400> SEQUENCE: 36

Val Arg Leu Pro Pro Pro Val Arg Leu Pro Pro Pro Val Arg Leu Pro
1               5                   10                  15

Pro Pro

<210> SEQ ID NO 37
<211> LENGTH: 13
<212> TYPE: PRT
<213> ORGANISM: Artificial Sequence
<220> FEATURE:
<223> OTHER INFORMATION: Chemically synthesized

<400> SEQUENCE: 37

Cys Gly Gly Gly Pro Lys Lys Lys Arg Lys Val Glu Asp
1               5                   10

<210> SEQ ID NO 38
<211> LENGTH: 18
<212> TYPE: PRT
<213> ORGANISM: Artificial Sequence
<220> FEATURE:
<223> OTHER INFORMATION: Chemically synthesized

<400> SEQUENCE: 38

Arg Gly Gly Arg Leu Ser Tyr Ser Arg Arg Arg Phe Ser Thr Ser Thr
1               5                   10                  15

Gly Arg

<210> SEQ ID NO 39
<211> LENGTH: 11
<212> TYPE: PRT
<213> ORGANISM: Artificial Sequence
<220> FEATURE:
<223> OTHER INFORMATION: Chemically synthesized

<400> SEQUENCE: 39

Tyr Gly Arg Lys Lys Arg Arg Gln Arg Arg
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Chemically synthesized
```

```
<400> SEQUENCE: 40

Gly Arg Lys Lys Arg Arg Gln Arg Arg Pro Pro Gln Gln
1               5                   10

<210> SEQ ID NO 41
<211> LENGTH: 9
<212> TYPE: PRT
<213> ORGANISM: Artificial Sequence
<220> FEATURE:
<223> OTHER INFORMATION: Chemically synthesized

<400> SEQUENCE: 41

Arg Lys Lys Arg Arg Gln Arg Arg Arg
1               5

<210> SEQ ID NO 42
<211> LENGTH: 13
<212> TYPE: PRT
<213> ORGANISM: Artificial Sequence
<220> FEATURE:
<223> OTHER INFORMATION: Chemically synthesized

<400> SEQUENCE: 42

Gly Arg Arg Arg Arg Arg Arg Arg Arg Pro Pro Gln
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Chemically synthesized

<400> SEQUENCE: 43

Gly Arg Lys Lys Arg Arg Gln Arg Arg Pro Trp Gln
1               5                   10

<210> SEQ ID NO 44
<211> LENGTH: 27
<212> TYPE: PRT
<213> ORGANISM: Artificial Sequence
<220> FEATURE:
<223> OTHER INFORMATION: Chemically synthesized

<400> SEQUENCE: 44

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 45
<211> LENGTH: 34
<212> TYPE: PRT
<213> ORGANISM: Artificial Sequence
<220> FEATURE:
<223> OTHER INFORMATION: Chemically synthesized

<400> SEQUENCE: 45

Asp Ala Ala Thr Ala Thr Arg Gly Arg Ser Ala Ala Ser Arg Pro Thr
1               5                   10                  15
```

Glu Arg Pro Arg Ala Pro Ala Arg Ser Ala Ser Arg Pro Arg Arg Pro
            20                  25                  30

Val Asp

<210> SEQ ID NO 46
<211> LENGTH: 16
<212> TYPE: PRT
<213> ORGANISM: Artificial Sequence
<220> FEATURE:
<223> OTHER INFORMATION: Chemically synthesized

<400> SEQUENCE: 46

Arg Gln Ile Lys Ile Trp Phe Gln Asn Arg Arg Met Lys Trp Lys Lys
1               5                   10                  15

<210> SEQ ID NO 47
<211> LENGTH: 9
<212> TYPE: PRT
<213> ORGANISM: Artificial Sequence
<220> FEATURE:
<223> OTHER INFORMATION: Chemically synthesized

<400> SEQUENCE: 47

Arg Arg Arg Arg Arg Arg Arg Arg Arg
1               5

<210> SEQ ID NO 48
<211> LENGTH: 4
<212> TYPE: PRT
<213> ORGANISM: Artificial Sequence
<220> FEATURE:
<223> OTHER INFORMATION: Chemically synthesized

<400> SEQUENCE: 48

Gly Thr Thr Gly
1

<210> SEQ ID NO 49
<211> LENGTH: 4
<212> TYPE: PRT
<213> ORGANISM: Artificial Sequence
<220> FEATURE:
<223> OTHER INFORMATION: Chemically synthesized

<400> SEQUENCE: 49

Thr Arg Leu Ser
1

<210> SEQ ID NO 50
<211> LENGTH: 4
<212> TYPE: PRT
<213> ORGANISM: Artificial Sequence
<220> FEATURE:
<223> OTHER INFORMATION: Chemically synthesized

<400> SEQUENCE: 50

Thr Glu Ala Ser
1

POLYPEPTIDES FOR TREATMENT OF CANCER

CROSS-REFERENCE TO RELATED APPLICATIONS

The present application is a 35 U.S.C. § 371 national phase application from, and claims priority to, PCT International Patent Application No. PCT/US2020/032638, filed May 13, 2020, which claims priority under 35 U.S.C. § 119(e) to U.S. Provisional Application No. 62/848,980, filed May 16, 2019, all of which are hereby incorporated by reference in their entireties herein.

BACKGROUND OF THE INVENTION

Cancer is characterized by abnormal and uncontrolled cell growth and proliferation, which may be followed by cell metastasis. Cancer is a leading cause of death worldwide, with the majority of cancer deaths caused by lung, breast, colorectal, stomach, brain, and liver cancers.

Lung cancer is the leading cause of cancer deaths in the U.S., among both men and women. Lung cancers are broadly classified into two types: small cell lung cancers (SCLC) and non-small cell lung cancers (NSCLC).

Breast cancer (BC) encompasses many distinct subtypes with unique pathologies and clinical ramifications. Comprising 15-20% of all breast cancer cases, triple negative breast cancer (TNBC) is characterized by absence of expression of the estrogen receptor (ER) or progesterone receptor (PR) and absence of overexpression of the human epidermal growth factor 2 receptor (HER2). This type of BC is typically more aggressive and resistant to endocrine therapies, resulting in a poorer prognosis with higher rates of relapse, metastases, and death. There are currently no targeted therapies available for TNBC.

While significant advancements have been made in cancer treatment, chemotherapy and radiation are the only available treatment options for patients with TNBC. There is thus a need in the art for novel compositions that can be used to treat TNBC, as well as other types of cancers including brain cancer and lung cancer. The present invention addresses this need.

BRIEF SUMMARY OF THE INVENTION

The present invention provides in one aspect a method of treating cancer in a subject. In certain embodiments, the method comprises administering to the subject a therapeutically effective amount of a polypeptide comprising, consisting essentially of, or consisting of amino acid residues 356-400 of co-activator of activator protein-1 and estrogen receptor (CAPER) isoform HCC1.3 (SEQ ID NO. 1). In certain embodiments, the method comprises administering to the subject a therapeutically effective amount of a polypeptide comprising, consisting essentially of, or consisting of amino acid residues 356-400 of CAPER isoform HCC1.4 (SEQ ID NO. 2).

The present invention provides in one aspect polypeptides, as well as pharmaceutical compositions comprising at least one such polypeptide, as well as kits comprising at least one such polypeptide and/or pharmaceutical composition, and an instructional material for use thereof. In certain embodiments, the polypeptide comprises, consists essentially of, or consists of amino acid residues 356-400 of co-activator of activator protein-1 and estrogen receptor (CAPER) isoform HCC1.3 (SEQ ID NO. 1). In certain embodiments, the polypeptide comprises, consists essentially of, or consists of amino acid residues 356-400 of CAPER isoform HCC1.4 (SEQ ID NO. 2). In certain embodiments, the polypeptide is derivatized at at least one amino acid residue, wherein the derivatization comprises methylation, amidation, or acetylation. In certain embodiments, the polypeptide is fused to a cell penetrating peptide.

BRIEF DESCRIPTION OF THE DRAWINGS

The following detailed description of specific embodiments of the invention will be better understood when read in conjunction with the appended drawings. For the purpose of illustrating the invention, specific embodiments are shown in the drawings. It should be understood, however, that the invention is not limited to the precise arrangements and instrumentalities of the embodiments shown in the drawings.

FIGS. 1A-1E are a set of graphs showing binding curves tested with CAPER peptides, full-length CAPER, and peptide controls. FIG. 1F is a graph showing binding curves using BLI. Amine reactive tips were conjugated with an anti-HIS tag antibody, his-tagged c-Jun was then bound to the tips. Tips were then saturated with the CAPER peptides or controls. In FIG. 1G signals generated are compared to full-length recombinant CAPER binding to the c-Jun receptor without the peptides present. n=3, p<0.05.

FIGS. 2A-2C are images for MDA-MB-231, BT549 and MCF10A cells treated with DMSO, CAPER peptide HCC1.3, CAPER peptide HCC1.4 and CAPER scrambled peptide for 1 hr. Cells were then stained with Alexa Fluor conjugated streptavidin to visualize the biotinylated peptides. Cells were also stained with DAPI DNA dye. Cells were imaged at 10× magnification using DAPI and GFP fluorescent cubes on an EVOS cell imager. In FIG. 2D the MDA-MB-231, BT549 and MCF10A cells were treated with DMSO, CAPER peptide HCC1.3, CAPER peptide HCC1.4 and CAPER scrambled peptide for 1 hr, fractionation was then performed to obtain proteins from the cytosolic and nuclear fractions. Western blotting was then performed using streptavidin to identify the biotinylated peptides. Loading controls used were GAPDH (cytosol) and Lamin A (nuclear).

FIG. 3A show graphs for cell counts for MDA-MB-231 and BT549 cells treated for 7 days with 20 µM of CAPER peptide HCC1.3, CAPER peptide HCC1.4, and CAPER Scrambled Peptide compared to DMSO and TAT only controls. ****p<0.0001, MDA-MB-231 treated with CAPER peptide HCC1.3 and HCC1.4 n=5, BT549 cells treated with CAPER peptide HCC1.3 and HCC1.4 n=4, Both cell lines treated with the Scrambled Peptide, n=3. FIG. 3B show images of MDA-MB-231 and BT549 cells treated with DMSO, TAT only control, CAPER peptide HCC1.3 and CAPER peptide HCC1.4 at 20 pM, 10× magnification using an EVOS cell imager.

FIG. 4A show set of graphs illustrating results from Caspase 3/7 assay for MDA-MB-231 and BT549 cells treated for 7 days with 20 µM of CAPER peptide HCC1.3, CAPER peptide HCC1.4, and Scrambled Peptide compared to DMSO and TAT only controls. **p<0.0001, *p<0.001**p<0.005, #p<0.05, MDA-MB-231 treated with CAPER peptide HCC1.3 and HCC1.4 n=5, BT549 cells treated with CAPER peptide HCC1.3 and HCC1.4 n=4, Both cell lines treated with the Scrambled Peptide, n=3. FIG. 4B shows results from Caspase 3/7 assay showing live, early apoptotic, apoptotic dead, and dead populations after treatment with DMSO, TAT control, CAPER peptide HCC1.3, CAPER peptide HCC1.4 and the CAPER scrambled peptide.

FIG. 5A show set of graphs illustrating results from the Annexin V assay for MDA-MB-231 and BT549 cells treated for 7 days with 20 µM of CAPER peptide HCC1.3, CAPER peptide HCC1.4, and CAPER Scrambled Peptide compared to DMSO and TAT only controls. **p<0.0001, *p<0.001, **p<0.005, *p<0.01, #p<0.05, MDA-MB-231 treated with CAPER peptide HCC1.3 and HCC1.4 n=5, BT549 cells treated with CAPER peptide HCC1.3 and HCC1.4 n=4, Both cell lines treated with the CAPER Scrambled Peptide n=3. FIG. 5B show results from the Annexin V assay showing live, early apoptotic, late apoptotic dead, and dead populations after treatment with DMSO, TAT control, CAPER peptide HCC1.3, CAPER peptide HCC1.4 and the CAPER scrambled peptide.

FIG. 6A show graphs for results from the Cell Cycle assay for MDA-MB-231 and BT-549 cells treated for 7 days with 20 µM of CAPER peptide HCC1.3, CAPER peptide HCC1.4, and CAPER Scrambled Peptide compared to DMSO and TAT only controls. p=not significant, n=3-5 per group. FIG. 6B show results from the Cell Cycle assay showing G1, S, and G2/M populations after treatment with DMSO, TAT control, CAPER peptide HCC1.3, CAPER peptide HCC1.4, and CAPER Scrambled Peptide.

FIG. 9A show results from the Annexin V assay for MCF10A cells treated for 7 days with 20 µM of CAPER peptide HCC1.3, CAPER peptide HCC1.4 compared to DMSO and TAT only controls, MDA-MB-231 treated with CAPER peptide HCC1.3 and HCC1.4 n=5, BT549 cells treated with CAPER peptide HCC1.3 and HCC1.4 n=4, Both cell lines treated with the CAPER Scrambled Peptide n=3. FIG. 9B show results from the Annexin V assay showing live, early apoptotic, late apoptotic dead, and dead populations after treatment with DMSO, TAT control, CAPER peptide HCC1.3 and CAPER peptide HCC1.4.

FIG. 10A are graphs showing binding curves tested with CAPER peptides, full-length CAPER and peptide controls. FIG. 10B is a graph showing inhibition of full length recombinant CAPER binding to ERα. In FIG. 10C signals generated are compared to full-length recombinant CAPER binding to the ERα.

FIG. 12A show results for MCF7 cells treated with 20 µM of CAPER peptide HCC1.3, CAPER peptide HCC1.4, compared to DMSO and TAT controls. FIG. 12B shows results from Caspase 3/7 assay showing live, early apoptotic, apoptotic dead, and dead populations after treatment with DMSO, TAT control, CAPER peptide HCC1.3, CAPER peptide HCC1.4.

FIG. 13A show results for MCF7 cells treated with 20 µM of CAPER peptide HCC1.3, CAPER peptide HCC1.4 compared to DMSO and TAT only controls. FIG. 13B show results for live, early apoptotic, late apoptotic dead, and dead populations after treatment with DMSO, TAT control, CAPER peptide HCC1.3 and CAPER peptide HCC1.4.

DETAILED DESCRIPTION OF THE INVENTION

Figure 1A:
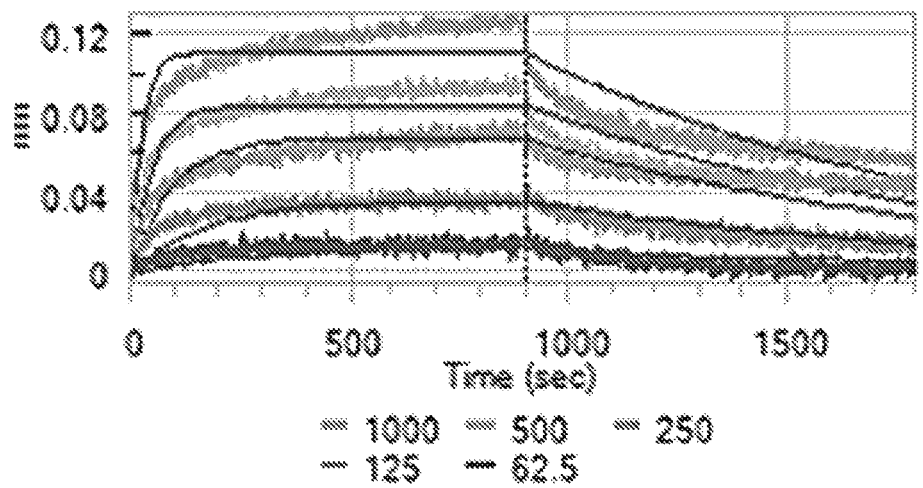
FIGS. 1A-1G show that CAPER peptides HCC1.3 and HCC1.4 bind to c-Jun with nM affinity and alter the binding of full-length recombinant CAPER.
Figure 1B:
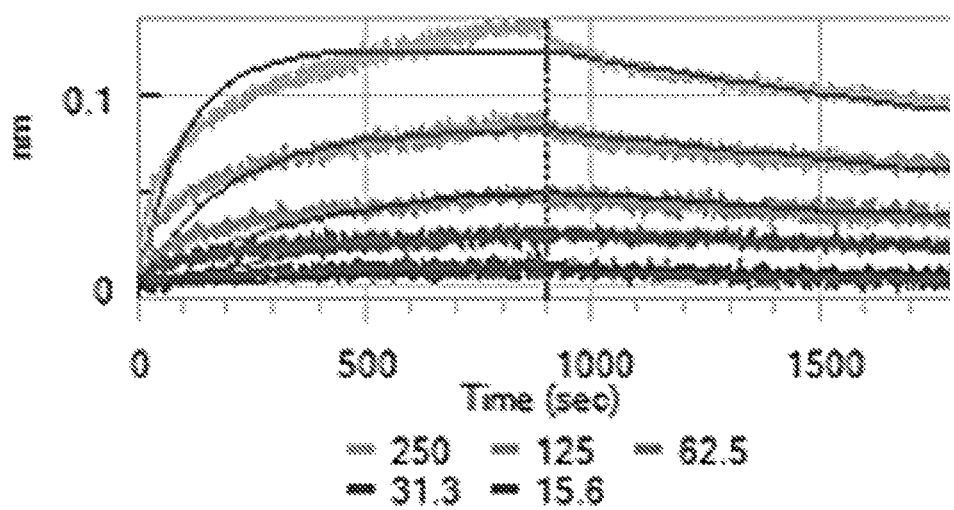
Figure 1C:
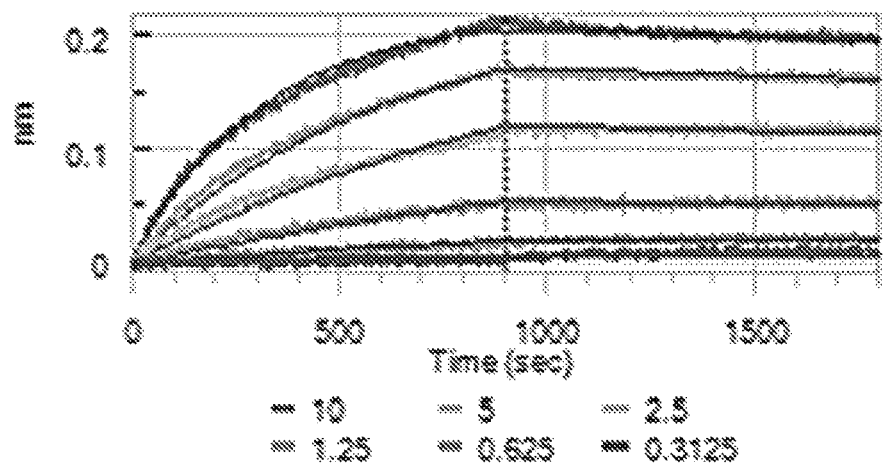
Figure 1D:
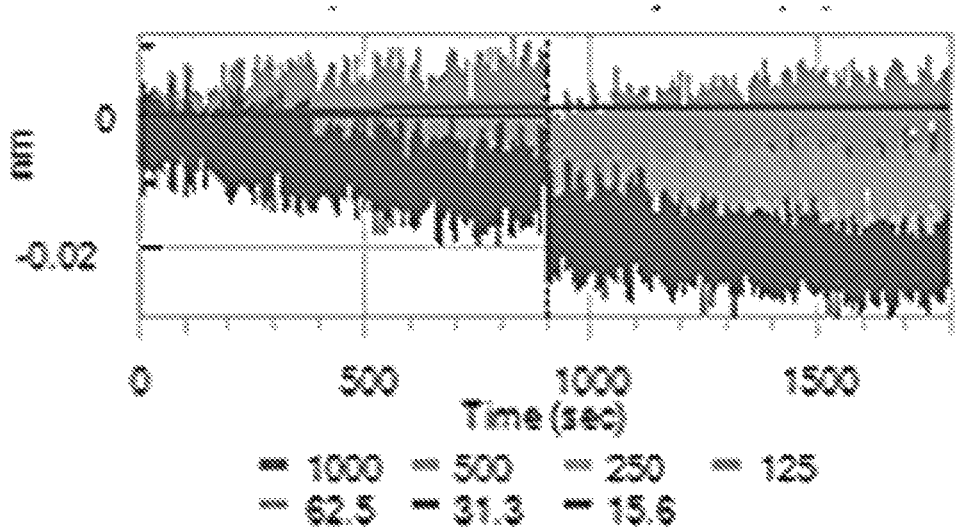
Figure 1E:
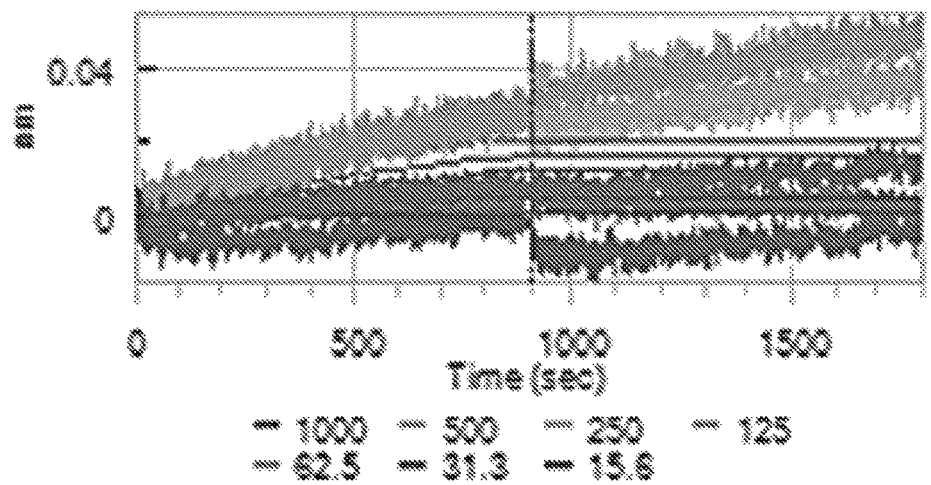

The present invention relates in part to the discovery that a polypeptide relating to the co-activator of activator protein-1 and estrogen receptor (CAPER) can be used as a novel therapeutic for treatment of various cancers. CAPER, also known as RNA binding protein-39 (Rbm39) and hepatocellular carcinoma-1.4 (HCC1.4), is a known regulator of steroid hormone receptor-mediated transcription and alternative splicing. For its co-activator activities, CAPER interacts with estrogen receptors ERα and ERβ, progesterone receptor (PR), and activator protein-1 (AP-1), binding to the c-Jun component specifically of the AP-1 dimer.

Without wishing to be bound by any particular theory, CAPER peptides shows at least two potential modes of action: 1.) a decrease in phosphorylated c-Jun, resulting in a modulation of both the AKT and NF-κB pathways with a decrease in pro-survival protein Bcl-2; and/or 2.) decrease in proteins associated with DNA repair, leading to impaired DNA repair function.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, oncology, and peptide chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of 20% or +10%, more preferably +5%, even more preferably +1%, and still more preferably +0.1% from the specified value, as such variations are appropriate to perform the disclosed methods.

As used herein, the term "cancer" is defined as disease characterized by the rapid and uncontrolled growth of aberrant cells. Cancer cells can spread locally or through the bloodstream and lymphatic system to other parts of the body. Examples of various cancers include but are not limited to, bone cancer, breast cancer, prostate cancer, ovarian cancer, cervical cancer, skin cancer, pancreatic cancer, colorectal cancer, renal cancer, liver cancer, brain cancer, lymphoma, leukemia, lung cancer, and the like. A tumor may be benign (benign tumor) or malignant (malignant tumor or cancer). Malignant tumors can be broadly classified into three major types. Malignant tumors arising from epithelial structures are called carcinomas, malignant tumors that originate from connective tissues such as muscle, cartilage, fat or bone are called sarcomas, and malignant tumors affecting hematopoietic structures (structures pertaining to the formation of blood cells) including components of the immune system, are called leukemias and lymphomas. Other tumors include, but are not limited to, neurofibromatosis.

As used herein, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount" or "therapeutically effective amount" or "pharmaceutically effective amount" of a compound are used interchangeably to refer to the amount of the compound that is sufficient to provide a beneficial effect to the subject to which the compound is administered.

As used herein, an "instructional material" includes a publication, a recording, a diagram, or any other medium of expression, which can be used to communicate the usefulness of the compound and/or composition of the invention in the kit for treating or preventing diseases or disorders recited herein. Optionally, or alternately, the instructional material may describe one or more methods of treating or preventing diseases or disorders in a cell or a tissue of a mammal. The instructional material of the kit of the invention may, for example, be affixed to a container, which contains the chemical compound and/or composition of the invention or be shipped together with a container, which contains the chemical composition and/or composition. Alternatively, the instructional material may be shipped separately from the container with the intention that the instructional material and the compound be used cooperatively by the recipient.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

The language "pharmaceutically acceptable carrier" includes a pharmaceutically acceptable salt, pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each salt or carrier must be "acceptable" in the sense of being compatible with the other ingredients of the formulation, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

As used herein, the term "pharmaceutical composition" refers to a mixture of at least one compound useful within the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound include, but are not limited to, intravenous, oral, aerosol, parenteral, ophthalmic, pulmonary and topical administration.

A "prophylactic" treatment is a treatment administered to a subject who does not exhibit signs of a disease or exhibits only early signs of the disease for the purpose of decreasing the risk of developing pathology associated with the disease.

The phrase "reduction of growth," as used herein, refers to any reduced growth, replication rate, or colony formation exhibited by a neoplastic cell, a cancer cell, or a tumor in response to some therapeutic agent, treatment, or clinical intervention, such as radiation. For example, a neoplastic cell may exhibit a reduction in the cell's growth rate or its ability to replicate and form colonies in vitro or in vivo (e.g., when implanted as a tumor in an animal) in response to radiation.

The phrase "reduction in viability," as used herein, refers to any reduction in survival exhibited by a neoplastic cell, a cancer cell, or a tumor in response to some chemotherapeutic agent, treatment, or clinical intervention, such as radiation. A neoplastic cell, a cancer cell, or a tumor may exhibit reduced viability in response to any such intervention by inhibition of progression of the cell through the cell cycle; damaged nucleic acids, proteins, or other macromolecules in a cell, induced terminal differentiation (senescence), in which the cell no longer replicates; inhibited cellular repair of nucleic acids; or increased rates of cell death by inducing apoptosis or "mitotic catastrophe"—a form of necrosis, when DNA damage levels are beyond those that can be effectively repaired.

A "therapeutic" treatment is a treatment administered to a subject who exhibits signs of pathology for the purpose of diminishing or eliminating those signs.

"Treating," as used herein, means reducing the frequency with which symptoms are experienced by a patient or subject, or administering an agent or compound to reduce the severity with which symptoms are experienced by a patient or subject. An appropriate therapeutic amount in any individual case may be determined by one of ordinary skill in the art using routine experimentation.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following abbreviations are used herein: ER=estrogen receptor, HER2=human epidermal growth factor receptor 2; PR=progesterone receptor, TNBC=triple negative breast cancer, CAPER=co-activator of activator protein-1 and estrogen receptor, AP-1=activator protein-1, and HCC=hepatocellular carcinoma.

Compositions

In one aspect, the invention provides a polypeptide for treating certain types of cancers. In certain embodiments, the polypeptide can be used to treat, prevent, and/or ameliorate a cancer such as but not limited to lung cancer, brain cancer, and breast cancer. In further embodiments, the breast cancer is a triple negative breast cancer. In certain embodiments, the breast cancer is an estrogen-positive breast cancer.

In certain embodiments, the polypeptide comprises amino acid residues 356-400 of CAPER isoform HCC1.3 (SEQ ID NO. 1). In other embodiments, the polypeptide consists essentially of the amino acid sequence of SEQ ID NO. 1. In yet other embodiments, the polypeptide consists of the amino acid sequence of SEQ ID NO. 1.

In certain embodiments, the polypeptide comprises amino acid residues 356-400 of CAPER isoform HCC1.4 (SEQ TD NO. 2). In other embodiments, the polypeptide consists essentially of the amino acid sequence of SEQ ID NO. 2. In yet other embodiments, the polypeptide consists of the amino acid sequence of SEQ ID NO. 2.

In certain embodiments, at least one amino acid within the polypeptide, and/or at carboxy-terminus and/or at the amino-terminus is methylated, amidated, acetylated, and/or substituted with any other chemical group without adversely affecting activity of the polypeptide within the methods of the invention.

In certain embodiments, the polypeptide is a fusion polypeptide, for example, wherein the polypeptide of the invention is fused to a cell penetrating peptide.

In certain embodiments, the cell penetrating peptide is an amphipathic peptide. In other embodiments, the cell penetrating peptide is a cationic peptide. In yet other embodiments, the cell penetrating peptide is provided herein (wherein lower case indicates D-stereochemistry):

```
Antennapedia (43-58)
                                         SEQ ID NO. 10
RQIKIWFQNRRMKWKK

BAC715-24
                                         SEQ ID NO. 11
PRPLPFPRPG

BMV Gag-(7-25)
                                         SEQ ID NO. 12
KMTRAQRRAAARRNRWTAR

BUFORIN II
                                         SEQ ID NO. 13
TRSSRAGLQFPVGRVHRLLRK

CADY
                                         SEQ ID NO. 14
GLWRALWRLLRSLWRLLWRA

CCMV Gag-(7-25)
                                         SEQ ID NO. 15
KLRTRAQRRAAARKNKRNTR

Cell Penetrating ARF Peptide (26-44)
                                         SEQ ID NO. 16
H-D-Arg-D-Arg-D-Arg-D-Arg-D-Arg-D-Arg-D-Arg-D-

Arg-D-Arg-Lys-Phe-Val-Arg-Arg-Ser-Arg-Pro-

Arg-Thr-Ala-Ser-Cys-Ala-Leu-Ala-Phe-Val-Asn-OH

D-TAT
                                         SEQ ID NO. 17
rrrqrrkkr

FHV COAT-(35-49)
                                         SEQ ID NO. 18
RRRRNRTRRNRRRVR hCT (9-32)
                                         SEQ ID NO. 19
LGTYTQDFNKFHTFPQTAIGVGAP

HIV-1 Rev (34-50)
                                         SEQ ID NO. 20
TRQARRNRRRRWRERQR

HN-1
                                         SEQ ID NO. 21
TSPLNIHNGQKL

HTLV-II Rex-(4-16)
                                         SEQ ID NO. 22
TRRQRTRRARRNR

K-FGF
                                         SEQ ID NO. 23
AAVALLPAVLLALLAP
```

-continued

Ku70  
SEQ ID NO. 24  
VPMLKPMLKE

MAP  
SEQ ID NO. 25  
KLALKLALHALKAALKLAKLALKLALKALKAALKLA

MPG (Pa)  
SEQ ID NO. 26  
GALFLAFLAAALSLMGLWSQPKKKRRV

MPG (Pb)  
SEQ ID NO. 27  
GALFLGFLGAAGSTMGAWSQPKKKRKV

P22 N-(14-30)  
SEQ ID NO. 28  
NAKTRRHERRRKLAIER

Pen2W2F  
SEQ ID NO. 29  
RQIKIFFQNRRMKFKK

Pep-1  
SEQ ID NO. 30  
KETWWETWWTEWSQPKKKRRV

Pep-7  
SEQ ID NO. 31  
SDLWEMMMVSLACQY plsl-1  
SEQ ID NO. 32  
RVIRVWFQNKRCKDKK pVEC  
SEQ ID NO. 33  
LLIILRRRIRKQAHAHSK

R7W  
SEQ ID NO. 34  
RRRRRRRW

RVG-9R  
SEQ ID NO. 35  
YTIWMPENPRPGTPCDIFTNSRGKRASNGGGGRRRRRRRRR

SAP  
SEQ ID NO. 36  
VRLPPPVRLPPPVRLPPP

SV-40 Large T-antigen Nuclear Localization Signal  
SEQ ID NO. 37  
CGGGPKKKRKVED SynB (1)  
SEQ ID NO. 38  
RGGRLSYSRRRFSTSTGR TAT (HIV-1 peptide)  
SEQ ID NO. 39  
YGRKKRRQRRR

TAT (HIV-1 (48-61))  
SEQ ID NO. 40  
GRKKRRQRRRPPQQ

TAT (HIV-1 (49-57))  
SEQ ID NO. 41  
RKKRRQRRR

TAT Derivative: R9-Tat  
SEQ ID NO. 42  
GRRRRRRRRRPPQ

TAT P59W  
SEQ ID NO. 43  
GRKKRRQRRRPWQ

Transportan  
SEQ ID NO. 44  
GWTLNSAGYLLGKINLKALAALAKKIL

VP-22  
SEQ ID NO. 45  
DAATATRGRSAASRPTERPRAPARSASRPRRPVD p-Antp  
SEQ ID NO. 46  
RQIKIWFQNRRMKWKK Arg9  
SEQ ID NO. 47  
R9 or functionally equivalent variants thereof.

In certain embodiments, the cell penetrating peptide is fused to the polypeptide via a linker.

In certain embodiments, the linker comprises polyethylene glycol chains (PEGs), peptides, and/or peptide nucleic acids (PNAs).

In certain embodiments, the linker is covalently linked to the N-terminus of the polypeptide. In other embodiments, the C-terminus of the linker is not GTTG (SEQ ID NO. 48). In yet other embodiments, the C-terminus of the linker is not TTG. In yet other embodiments, the C-terminus of the linker is not TG. In yet other embodiments, the C-terminus of the linker is not G.

In certain embodiments, the linker is covalently linked to the C-terminus of the polypeptide. In other embodiments, the N-terminus of the linker is not TRLS (SEQ ID NO. 49). In yet other embodiments, the N-terminus of the linker is not TRL. In yet other embodiments, the N-terminus of the linker is not TR. In yet other embodiments, the N-terminus of the linker is not T.

In certain embodiments, the linker is covalently linked to the C-terminus of the polypeptide. In other embodiments, the N-terminus of the linker is not TEAS (SEQ ID NO. 50). In yet other embodiments, the N-terminus of the linker is not TEA. In yet other embodiments, the N-terminus of the linker is not TE. In yet other embodiments, the N-terminus of the linker is not T.

In certain embodiments, the cell penetrating peptide is covalently linked to the N-terminus of the polypeptide. In other embodiments, the C-terminus of the cell penetrating peptide is not GTTG (SEQ ID NO. 48). In yet other embodiments, the C-terminus of the cell penetrating peptide is not TTG. In yet other embodiments, the C-terminus of the cell penetrating peptide is not TG. In yet other embodiments, the C-terminus of the cell penetrating peptide is not G.

In certain embodiments, the cell penetrating peptide is covalently linked to the C-terminus of the polypeptide. In other embodiments, the N-terminus of the cell penetrating peptide is not TRLS (SEQ ID NO. 49). In yet other embodiments, the N-terminus of the cell penetrating peptide is not TRL. In yet other embodiments, the N-terminus of the cell penetrating peptide is not TR. In yet other embodiments, the N-terminus of the cell penetrating peptide is not T.

In certain embodiments, the cell penetrating peptide is covalently linked to the C-terminus of the polypeptide. In other embodiments, the N-terminus of the cell penetrating peptide is not TEAS (SEQ ID NO. 50). In yet other embodiments, the N-terminus of the cell penetrating peptide is not TEA. In yet other embodiments, the N-terminus of the cell penetrating peptide is not TE. In yet other embodiments, the N-terminus of the cell penetrating peptide is not T.

In certain embodiments, the peptide linker comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids.

In certain embodiments, the linker comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 ethylene glycol (—CH$_2$CH$_2$O— or —OCH$_2$CH$_2$—) units.

In another aspect, the invention provides a pharmaceutical composition comprising the polypeptide of the invention.

Methods

In one aspect, the invention provides a method for treating cancer in a subject in need thereof. In certain embodiments, the method comprises administering to the subject a therapeutically effective amount of a polypeptide of the invention. In other embodiments, the cancer includes lung cancer, breast cancer, and/or brain cancer. In yet other embodiments, the breast cancer is a triple negative breast cancer. In yet other embodiments, the breast cancer is an estrogen-positive breast cancer.

In certain embodiments, the polypeptide of the invention is as described elsewhere herein. In other embodiments, the polypeptide binds to c-Jun component of activator protein-1 (AP-1) with an equilibrium dissociation constant (K$_D$) ranging from about 5 nM to about 50 nM. In yet other embodiments, the binding of polypeptide to c-Jun component of AP-1 inhibits the binding of full-length CAPER protein to the c-Jun component of AP-1. In yet other embodiments, the polypeptide binds to ERα with an equilibrium dissociation constant (K$_D$) ranging from about 5 nM to about 50 nM. In yet other embodiments, the binding of the polypeptide to ERα inhibits the binding of full-length CAPER protein to ERα.

In certain embodiments, the administering induces apoptosis in cancer cells preferentially over non-cancerous cells. In certain embodiments, the administering induces DNA damage in cancer cells. In certain embodiments, administering does not induce DNA damage in non-cancerous cells.

In certain embodiments, the cancer cells are lung cancer cells, breast cancer cells and/or brain cancer cells. In an exemplary embodiment, upon treatment with the polypeptide of the invention, both MDA-MD-231 and BT549 TNBC cell lines show a significant decrease in cell number and an increase in apoptotic cells with no significant change to non-tumorigenic cell line MCF10A.

In certain embodiments, the polypeptide is administered as part of a pharmaceutical composition.

In certain embodiments, the subject is not administered with any additional chemotherapeutic agent and/or anti-cell proliferation agent. In certain embodiments, the subject is not administered any additional chemotherapeutic agent or anti-cell proliferation agent in an amount sufficient to treat, prevent, and/or ameliorate the cancer in the subject.

In certain embodiments, the method further comprising administering to the subject at least one additional agent selected from the group consisting of radiation, a chemotherapeutic agent, an anti-cell proliferation agent, a gene therapy agent, and an immunotherapy agent. In certain embodiments, the polypeptide and the at least one additional compound are co-administered to the subject. In certain embodiments, the polypeptide and the at least one additional compound are coformulated. In certain embodiments, the at least one additional compound is selected from the group consisting of taxotere, cyclophosphamide, paclitaxel, fluorouracil, doxorubicin, cycloheximide, olaparib, and temozolomide In certain embodiments, the composition is formulated as part of an extended-release formulation. In other embodiments, the composition is administered to the subject by at least one route selected from the group consisting of inhalation, oral, rectal, vaginal, parenteral, topical, transdermal, pulmonary, intranasal, buccal, sublingual, ophthalmic, intrathecal, intravenous, and intragastrical.

In certain embodiments, the subject is a mammal. In other embodiments, the subject is a human.

Kit

In yet another aspect, the invention provides a kit comprising a composition comprising a polypeptide of the invention, and an instructional material for use thereof, wherein the instructional material comprises instructions for treating cancer in a subject in need thereof.

In certain embodiments, the composition is as described elsewhere herein. In certain embodiments, the polypeptide is as described elsewhere herein.

Combination Therapies

In certain embodiments, the compounds of the present invention are useful in the methods of present invention in combination with one or more additional compounds useful for treating the diseases or disorders contemplated within the invention. These additional compounds may comprise compounds of the present invention or compounds, e.g., commercially available compounds, known to treat, prevent, or reduce the symptoms of the diseases or disorders contemplated within the invention.

Non-limiting examples of additional compounds contemplated within the invention include chemotherapeutic agents, anti-cell proliferation agents, gene therapy agents, immunotherapy agents, and radiation. In certain embodiments, the compounds contemplated within the invention can be used in combination with one or more compounds selected from, but not necessarily limited to, the group consisting of taxotere, cyclophosphamide, paclitaxel, fluorouracil, doxorubicin, cycloheximide, olaparib and temozolomide. In other embodiments, the compounds contemplated within the invention can be used in combination with any chemotherapeutic, gene therapy or immunotherapy compound or treatment regimen known in the art. In yet other embodiments, the compounds contemplated within the invention can be used in combination with chemotherapeutic compounds known to treat cancer and/or radiation therapy.

The compounds contemplated within the invention may be administered before, during, after, or throughout administration of any therapeutic agents used in the treatment of a subject's disease or disorder.

A synergistic effect may be calculated, for example, using suitable methods such as, for example, the Sigmoid-E$_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the patient either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions useful within the present invention to a patient, preferably a mammal, more preferably a human, may be carried out using known procedures, at dosages and for periods of time effective to treat a disease or disorder in the patient. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the present invention is from about 1 and 5,000 mg/kg of body weight/per day. One of ordinary skill in the art is able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the present invention employed in the pharmaceutical composition at levels lower than that required in order to achieve the desired therapeutic effect and gradually increase the dosage until the desired effect is achieved.

In particular embodiments, it is advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the present invention are dictated by and directly dependent on the unique characteristics of the therapeutic compound and the particular therapeutic effect to be achieved, and the limitations inherent in the art of compounding/formulating such a therapeutic compound for the treatment of a disease or disorder in a patient.

In certain embodiments, the compositions useful within the invention are formulated using one or more pharmaceutically acceptable excipients or carriers. In certain embodiments, the pharmaceutical compositions of the present invention comprise a therapeutically effective amount of a compound useful within the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate, or gelatin.

In certain embodiments, the compositions useful within the invention are administered to the patient in dosages that range from one to five times per day or more. In other embodiments, the compositions useful within the invention are administered to the patient in range of dosages that include, but are not limited to, once every day, every two days, every three days to once a week, and once every two weeks. It is readily apparent to one skilled in the art that the frequency of administration of the various combination compositions useful within the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physician taking all other factors about the patient into account.

Compounds for administration may be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 3050 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments there between.

In some embodiments, the dose of a compound is from about 1 mg and about 2,500 mg. In some embodiments, a dose of a compound of the present invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating a disease or disorder) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the drug is therapeutically active at a circulating and/or tissue concentration of about 1, 2, 4, 6, 8, 10, 12, 14, 16, 18, 20, 25, 30, 35, 40, 45 or 50 µM.

In certain embodiments, the present invention is directed to a packaged pharmaceutical composition comprising a container holding a therapeutically effective amount of a compound of the present invention, alone or in combination with a second pharmaceutical agent; and instructions for using the compound to treat, prevent, or reduce one or more symptoms of a disease or disorder in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like. They may also be combined where desired with other active agents, e.g., other anti-tumor agents.

The term "container" includes any receptacle for holding the pharmaceutical composition. For example, in certain embodiments, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Routes of administration of any of the compositions of the present invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral administration, particularly suitable are tablets, dragees, liquids, drops, or capsules, caplets and gelcaps. The compositions intended for oral use may be prepared according to any method known in the art and such compositions may contain one or more agents selected from the group consisting of inert, non-toxic pharmaceutically acceptable excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulfate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Parenteral Administration

For parenteral administration, the compounds may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the present invention may be administered in the form of microparticles, for example, by injection or in the form of wafers or discs by implantation.

In certain embodiments, the compounds of the present invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, include a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound depends on the age, sex and weight of the patient, the current medical condition of the patient and the progression of the disease or disorder in the patient being treated. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

The compounds for use in the method of the present invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions with art-recognized alternatives and using no more than routine experimentation, are within the scope of the present application.

It should be understood that the method and compositions that would be useful in the present invention are not limited to the particular formulations set forth in the examples. The following examples are put forth so as to provide those of ordinary skill in the art with a complete disclosure and description of how to make and use the composition and therapeutic methods of the invention, and are not intended to limit the scope of what the inventor regard as his invention.

The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Materials

Cell lines MCF7, MDA-MB-231, BT549 and MCF10A were purchased from American Type Culture Collection (ATCC, Manassas, VA). The following primary antibodies were purchased from Cell Signaling Technology (Danvers, MA) Bcl-2, phospho-c-Jun Serine 73, phospho-c-Jun Serine 63, c-Jun, RAD51, NF-KB, Phospho-NF-KB, AKT, Phospho-AKT, Cyclin D1, c-abl. Anti-GAPDH antibody was purchased from Fitzgerald.

Methods

Cell Culture

MCF7 cells were routinely cultured in minimum essential media (MEM, cat #11095-080, Life Technologies) containing 10% fetal bovine serum (FBS, cat #16140, Life Technologies), 1% penicillin/streptomycin (cat #15140, Life Technologies), 1% sodium pyruvate (cat #11360-070, Life Technologies) and 0.01 mg/mL insulin (cat #I0516, Sigma-Aldrich). MDA-MB-231 cells were cultured in Dulbecco minimum essential medium (DMEM) (cat #11965, Life Technologies, Carlsbad, CA), containing 10% fetal bovine serum (FBS, cat #16140, Life Technologies), 1% penicillin/streptomycin (cat #15140, Life Technologies) and 1% sodium pyruvate (cat #11360-070, Life Technologies). BT549 cells were cultured in RPMI 1640 (cat #A10491, Life Technologies), supplemented with 10% FBS, 0.023 IU/mL insulin (cat #I0516, Sigma-Aldrich) and 1% penicillin/streptomycin. MCF10A cells were cultured in DMEM/F12 medium (cat #, Life Technologies) supplemented with 5% horse serum (Cat #), 20 µg/mL of EGF (cat #AF-100-12, Peprotech, Rocky Hill, NJ), 0.5 mg/mL hydrocortisone (cat #H0888, Sigma-Aldrich), 10 µg/mL insulin, 100 ng/mL cholera toxin (cat #c8052, Sigma-Aldrich) and 1% penicillin/streptomycin.

Peptides

Peptides were custom synthesized by LifeTein (Somerset, NJ) as crude purity with a single biotin on the N-terminus. Peptides were stored lyophilized at −70° C. until reconstitution in sterile water containing 2% DMSO (Fisher). The concentration of the reconstituted peptides was verified by absorbance using a Nanodrop 2000 (Thermo Scientific, Waltham, MA) at A280.

Sequences Used:

```
SEQ ID NO. 1: CAPER peptide HCC1.3 (amino acid residues 356-400)
RLQLMARLAEGTGLQIPPAAQQALQMSGSLAFGAVADLQTRLSQQ SEQ ID NO. 2: CAPER peptide HCC1.4 (amino acid residues 356-400)
RLQLMARLAEGTGLQIPPAAQQALQMSGSLAFGAVAEFSFVIDLQ SEQ ID NO. 3: CAPER peptide Scrambled
VGDALQGLRLFSTQASIGAQMEQLAAQPLRAGQMLQLAQASPLRT SEQ ID NO. 4: TAT Control Peptide:
YGRKKRRQRRR SEQ ID NO. 5: CAPER peptide HCC1.3 TAT
YGRKKRRQRRRRLQLMARLAEGTGLQIPPAAQQALQMSGSLAFGAVADLQTRLSQQ SEQ ID NO. 6: CAPER peptide HCC1.4 TAT:
YGRKKRRQRRRRLQLMARLAEGTGLQIPPAAQQALQMSGSLAFGAVAEFSFVIDLQ SEQ ID NO. 7: CAPER peptide Scrambled TAT
YGRKKRRQRRRVGDALQGLRLFSTQASIGAQMEQLAAQPLRAGQMLQLAQASPLRT SEQ ID ND. 8: CAPER isoform HCC1.3
            10         20         30         40         50
    MADDIDIEAM LEAPYKKDEN KLSSANGHEE RSKKRKKSKS RSRSHERKRS 60         70         80         90        100
    KSKERKRSRD RERKKSKSRE RKRSRSKERR RSRSRSRDRR FRGRYRSPYS 110        120        130        140        150
    GPKFNSAIRG KIGLPHSIKL SRRRSRSKSP FRKDKSPVRE PIDNLTPEER 160        170        180        190        200
    DARTVFCMQL AARIRPRDLE EFFSTVGKVR DVRMISDRNS RRSKGIAYVE 210        220        230        240        250
    FVDVSSVPLA IGLTGQRVLG VPIIVQASQA EKNR1VIAN  NLQKGSAGPM 260        270        280        290        300
    RLYVGSLHFN ITEDMLRGIF EPFGRIESIQ LMMDSETGRS KGYGFITFSD 310        320        330        340        350
    SECAKKALEQ LNGFELAGRP MKVGHVTERT DASSASSFLD SDELERTGID 360        370        380        390        400
    LGTTGRLQLM ARLAEGTGLQ IPPAAQQALQ MSGSLAFGAV ADLQTRLSQQ 410        420        430        440        450
    TEASALAAAA SVQPLATQCF QLSNMFNPQT EEEVGWDTEI KDDVIEECNK 460        470        480        490        500
    HGGVIHIYVD KNSAQGNVYV KCPSIAAAIA AVNALHGRWF AGKMITAAYV 510        520
    PLPTYHNLFP DSMTATQLLV PSRR
```

-continued

```
SEQ ID NO. 9: CAPER isoform HCC1.4
         10         20         30         40         50
MADDIDIEAM LEAPYKKDEN KLSSANGHEE RSKKRKKSKS RSRSHERKRS 60         70         80         90        100
KSKERKRSRD RERKKSKSRE RKRSRSKERR RSRSRSRDRR FRGRYRSPYS 110        120        130        140        150
GPKFNSAIRG KIGLPHSIKL SRRRSRSKSP FRKDKSPVRE PIDNLTPEER 160        170        180        190        200
DARTVFCMQL AARIRPRDLE EFFSTVGKVR DVRMISDRNS RRSKGIAYVE 210        220        230        240        250
FVDVSSVPLA IGLTGQRVLG VPIIVQASQA EKNR1VIAN NLQKGSAGPM 260        270        280        290        300
RLYVGSLHFN ITEDMLRGIF EPFGRIESIQ LMMDSETGRS KGYGFITFSD 310        320        330        340        350
SECAKKALEQ LNGFELAGRP MKVGHVTERT DASSASSFLD SDELERTGID 360        370        380        390        400
LGTTGRLQLM ARLAEGTGLQ IPPAAQQALQ MSGSLAFGAV AEFSFVIDLQ 410        420        430        440        450
TRLSQQTEAS ALAAAASVQP LATQCFQLSN MFNPQTEEEV GWDTEIKDDV 460        470        480        490        500
IEECNKHGGV IHIYVDKNSA QGNVYVKCPS IAAAIAAVNA LHGRWFAGKM 510        520
ITAAYVPLPT YHNLFPDSMT ATQLLVPSRR
```

Binding Kinetics

The binding kinetics of the peptides and full-length recombinant CAPER (R&D Systems, Minneapolis, MN) with the c-Jun (Abcam, Cambridge, MA) were determined using biolayer interferometry (BLI) on the Octet HTX system (Pall ForteBio, Fremont, CA). Amine Reactive 2nd Generation biosensors (cat #18-5092, Pall ForteBio) were activated with 1-Ethyl-3-[3-dimethylaminopropyl] carbodiimide hydrochloride and N-hydroxysulfosuccinimide (EDC/NHS) (Amine Coupling Kit II, Cat #ACK-001-025, Sierra Sensors, Billerica, MA) and conjugated with an anti-his tag antibody. The reaction was then quenched with 1M ethanolamine (Amine Coupling Kit II, Cat #ACK-001-025, Sierra Sensors). His-tagged recombinant c-Jun was then bound to the tips. The peptides were tested at a series of 2-fold dilutions including a buffer blank. The binding of full-length recombinant CAPER was also tested. Association and dissociation steps were performed for 900s each in 1×HBS-EP+ buffer (cat #BR100669, GE Healthcare Lifesciences, Pittsburgh, PA) supplemented with 450 mM NaCl (Sigma). The background was subtracted from each run and kinetics data was analyzed using ForteBio's Data Analysis Software version 10.0.3.1 using a 1:1 model.

Competition Assays

Competition assays were determined using BLI on the Octet HTX system (Pall ForteBio, Fremont, CA). Amine Reactive 2nd Generation biosensors (cat #18-5092, Pall ForteBio) were activated with 1-Ethyl-3-[3-dimethylaminopropyl] carbodiimide hydrochloride and N-hydroxysulfosuccinimide (EDC/NHS) (Amine Coupling Kit II, Cat #ACK-001-025, Sierra Sensors, Billerica, MA) and conjugated with an anti-his tag antibody. The reaction was then quenched with 1M ethanolamine (Amine Coupling Kit II, Cat #ACK-001-025, Sierra Sensors). Recombinant c-Jun containing a his-tag was then bound to the tips. The peptides were allowed to saturate the receptor at a concentration of 10× the KD of each peptide. After receptor saturation binding of full-length CAPER to the receptor was measured and the signal was compared back to full-length CAPER binding to the receptor in the absence of the peptide. Binding steps were performed for 900s each in 1× HBS-EP+ buffer (cat #BR100669, GE Healthcare Lifesciences, Pittsburgh, PA) supplemented with 450 mM NaCl (Sigma). The background was subtracted from each run and the signal was represented as a % inhibition compared to full-length CAPER binding in the absence of the peptide.

Immunofluorescence

Coverslips were placed at the bottom of a 6-well plate, and 150,000 cells/well were added. The plates were incubated overnight at 37° C. with 5% $CO_2$ to allow the cells to attach. The next day, cells were treated with the peptides at 10 µM for 1 hr. After the indicated time, media was removed, and the cells were rinsed three times with PBS, and the cells were fixed with ice cold 70% MeOH at −20 C or 10 min. Cells were washed 3 times with PBS and then incubated with Streptavidin, Alexa-fluor 488 conjugate (cat #532354, Life Technologies) for 1 hr at 37° C. Cells were then mounted with Prolong Gold Antifade Mounant with DAPI (cat #P36941, Life Technologies). Slides were visualized using the EVOS cell imaging system (Thermo Fisher) with a DAPI fluorescent light cube, GFP fluorescent light cube and imaged on an EVOS cell imager using 10× magnification.

Fractionation

MDA-MB-231, BT549, and MCF10A cells were added to 10 cm dishes and allowed to attach overnight in a 37 C with 5% $CO_2$ incubator. The next day, cells were treated with the peptides at 20 µM for 1 hr. After the indicated time, media was removed and the cells were rinsed with PBS and trypzined using 0.05% trypsin. The cells were then washed 2 times with PBS and a hypotonic lysis buffer comprised of 10 mM HEPES, 1.5 mM $MgCl_2$, 10 mM KCl, 1 mM DTT, 0.1 mM EDTA, with protease and phosphatase inhibitors was added. The cells were allowed to sit on ice for 10 min and then passed through a needle, and allowed to sit on ice and additional 10 min. The lysate was then centrifuged for 10 min at 13,000 rpm. The supernatant was removed and added to a fresh tube (cytosolic fraction). The pellet was then rinsed twice with PBS, after the final rinse, the PBS was removed and the pellet was taken up in a hypertonic buffer containing 20 mM HEPES, 1.5 mM $MgCl_2$, 1 mM EDTA, 1 mM DTT, 20% glycerol pH 7.9 with the addition of protease and phosphatase inhibitors. The lysate was then sonicated at 30 amp and homogenized. The lysate was then allowed to sit on ice for 30 min, with periodic vortexing. The lysate was then centrifuged for 10 min and the supernatant was added to a fresh tube (nuclear fraction). All lysates were then stored at −70° C. until use.

Treatment of Cell Lines with CAPER Peptides and Cell Count

MCF7 cells were switched to phenol free DMEM (cat #, 11054-020, Life Technologies), with 10% charcoal stripped FBS (cat #A33821-01, Life Technologies), 24 hrs prior to plating. After the starvation period, the cells were plated onto mm plates at cells/plate and allowed to adhere overnight. The next day cells were dosed with 20 µM of CAPER peptides along with a DMSO and TAT only controls with and without estradiol (E2) (cat #, Sigma). Cells were pretreated with the peptide 4 hrs before the E2 was added. Cells were dosed daily for 7 days. At the end of the 7 day dosing period, floating cells were collected and adherent cells were trypsinized and counted via a hemocytometer MDA-MB-231, BT549, and MCF10A cells were plated onto 10 cm plates at 50,000 cells per plate, 100,000 cells per plate and 25,000 cells, respectively. The cells were allowed to adhere overnight, the next day cells were with 20 µM of CAPER peptides along with a DMSO and TAT only controls. Cells were dosed daily for 7 days. At the end of the 7 day dosing period, floating cells were collected and adherent cells were trypsinized and counted via a hemocytometer.

Apoptosis Assays

Apoptosis was evaluated using both a Muse Caspase 3/7 kit (cat #MCH100108, EMD Millipore) and Muse Annexin V kit (Millipore cat #). Cells were treated for 7 days as described elsewhere herein, at the end of the 7 day dosing period, floating cells were collected and attached cells were washed 1× with PBS and then trypsinized with 0.05% trypsin. Cells were collected and combined with the floating cells. Cells were then counted and diluted to 20,000 cells/mL. For the caspase assay, 50 µL of cells were then incubated with the Muse Caspase 3/7 reagent at 37° C. for 30 min. After incubation 5 µL of 7-ADD dye was added and incubated for 5 min at room temperature. Cells were then analyzed on the Muse Cell Analyzer (Millipore). For the Annexin V assay, 100 µL of cells was then added to 100 µL of Annexin V reagent for 30 min at room temperature. Cells were then analyzed on the Muse Cell Analyzer (Millipore).

Cell Cycle Assay

MDA-MB-231 and BT549 cells were synchronized using nocodazole (cat #Sigma-Aldrich) for 24 hours. The floating cells were then aspirated off and the plate was rinsed with media to collect the loosely attached cells (G2/M fraction). The cells were then plated as described above. A fraction of the treated cells was processed for cell cycle to confirm synchronization. Cells were then treated for 7 days as described above, at the end of the 7 day dosing period, floating cells were collected and attached cells were washed 1× with PBS and then trypsinized with 0.05% trypsin. Cells were collected and combined with the floating cells. Cells were counted and diluted according to the Muse Cell Cycle Kit (cat #MCH100106, EMD Millipore) instructions and samples were then read on the Muse Cell Analyzer.

Western Blot Analysis

After the 7 day treatment period, cells were harvested and washed with cold PBS. Cells were than lysed in complete RIPA buffer containing protease inhibitor cocktail (Roche) and phosphatase inhibitors. Samples were placed on ice and sonicated for 30s and then centrifuged 10 min at 10,000×g at 4° C. After centrifugation, the supernatant was removed and stored at −70° C. until use. Total protein concentration was determined by performing a BCA assay and equal amounts of protein were added to the wells of a SDS-PAGE gel and then transferred to a nitrocellulose membrane. Membranes were blocked for 1 hr at room temperature with either 5% BSA or 5% non-fat milk in 1×TBST buffer. After incubation, membranes were incubated with the primary antibody overnight at 4° C. The next day, membranes were washed 3× for 10 min each with TBST and then incubated with appropriate secondary antibody for 1 hr. Membranes were washed 3× for 10 min each with TBST and then read using the Licor Odyssey Imager. Licor Image Studio Version was used to quantify the bands. Protein of interest was then normalized to the GAPDH protein loading control. Each probe was repeated for a minimum of three independent runs.

Statistical Analysis

All data were expressed as mean plus/minus S.E.M and differences between groups were evaluated by either unpaired Student's t-test or one-way ANOVA. Statistical significance is marked as **$p<0.0001$, *$p<0.001$, **$p<0.005$, *$p<0.01$, #$p<0.05$.

Example 1: CAPER Peptides Bind to c-Jun with nM Affinity and Alter Binding of Recombinant Full-Length CAPER with c-Jun Binding kinetics of the peptides were determined and the association constants and dissociation constants of each were calculated. The $K_D$ of CAPER peptide HCC1.4 and CAPER peptide HCC1.3 were determined to be 25.56 and 8.89 nM, respectively, whereas the $K_D$ of the CAPER scrambled peptide and TAT only control could not be determined (FIGS. 1A-1E and Table. 1).

Figure 1F:
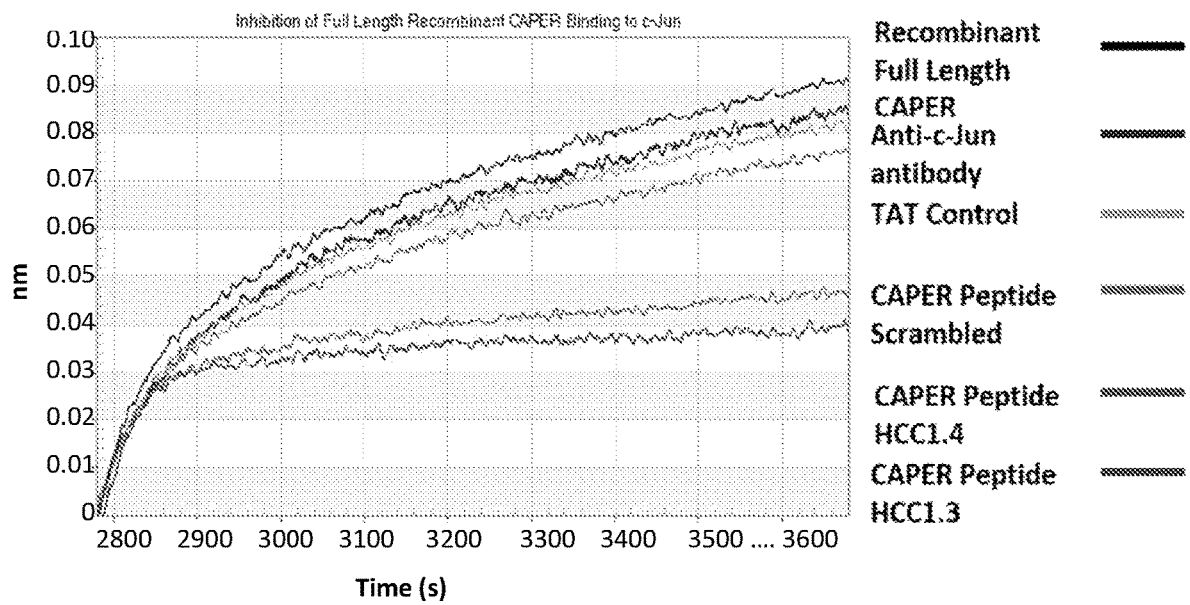
Figure 1G:
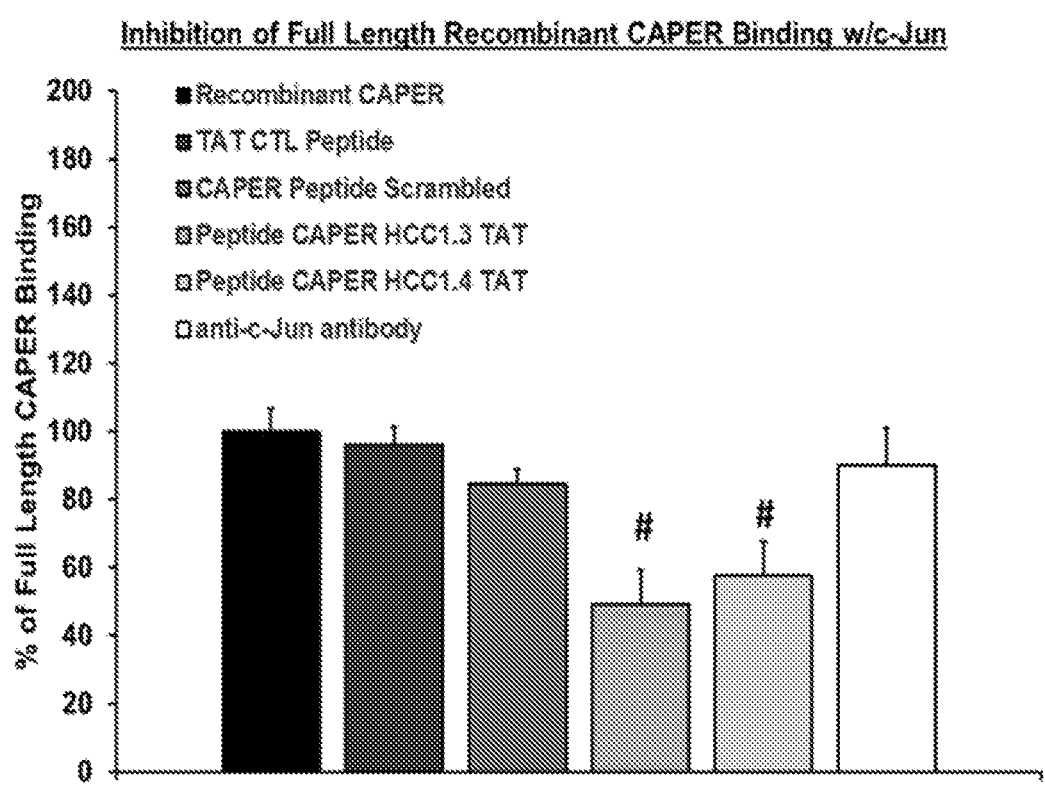

To test if the CAPER peptides might prevent full-length recombinant CAPER from binding to c-Jun a competition assay was conducted. Results show that when the c-Jun receptor is saturated with CAPER peptides HCC1.3 and HCC1.4, full-length recombinant CAPER binding is inhibited by 50.7% and 42.2%, respectively. The scrambled peptide and the anti-c-Jun antibody show no significant change in CAPER binding to c-Jun (FIG. 1F).

TABLE 1

| | Binding to c-Jun | | | | |
|---|---|---|---|---|---|
| | KD (nM) | K on (1/Ms) | K off (1/s) | $X^2$ | $R^2$ |
| CAPER Peptide HCC1.4 | 25.56 | 3.83E+04 | 9.80E−04 | 0.1791 | 0.9555 |
| CAPER Peptide HCC1.3 | 8.89 | 3.79E+04 | 3.37E−04 | 0.0928 | 0.9823 |
| Recombinant Full-Length CAPER HCC1.3 | 0.18 | 3.12E+05 | 5.66E−05 | 0.0652 | 0.9968 |
| CAPER Scrambled Peptide | N.D. | | | | |
| TAT Control Peptide | N.D. | | | | |

Example 2: Peptides Efficiently Enter TNBC Cells and MCF10A Cells

Figure 2A:
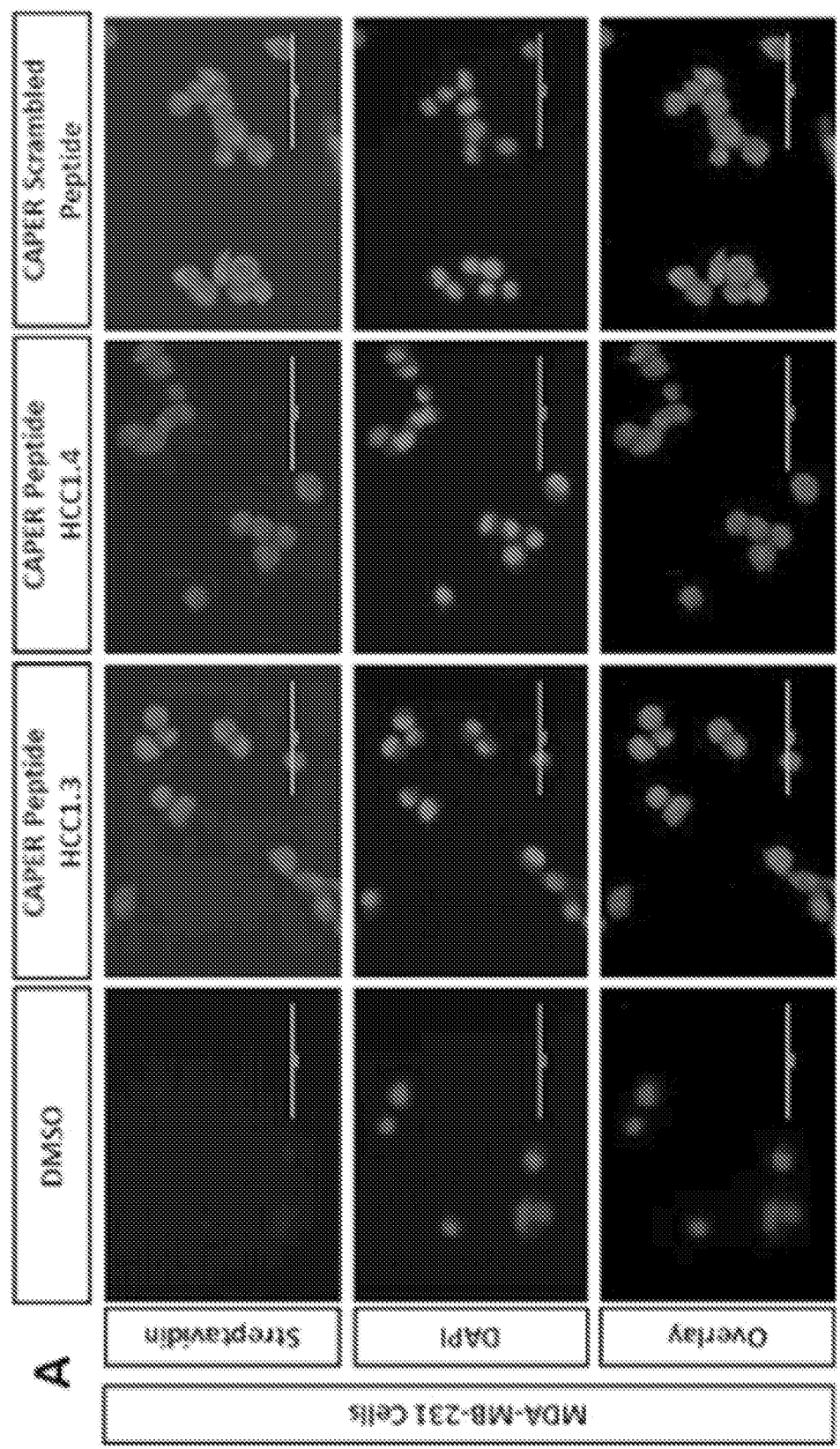
FIGS. 2A-2D show CAPER peptides enter cells and the nucleus.
Figure 2B:
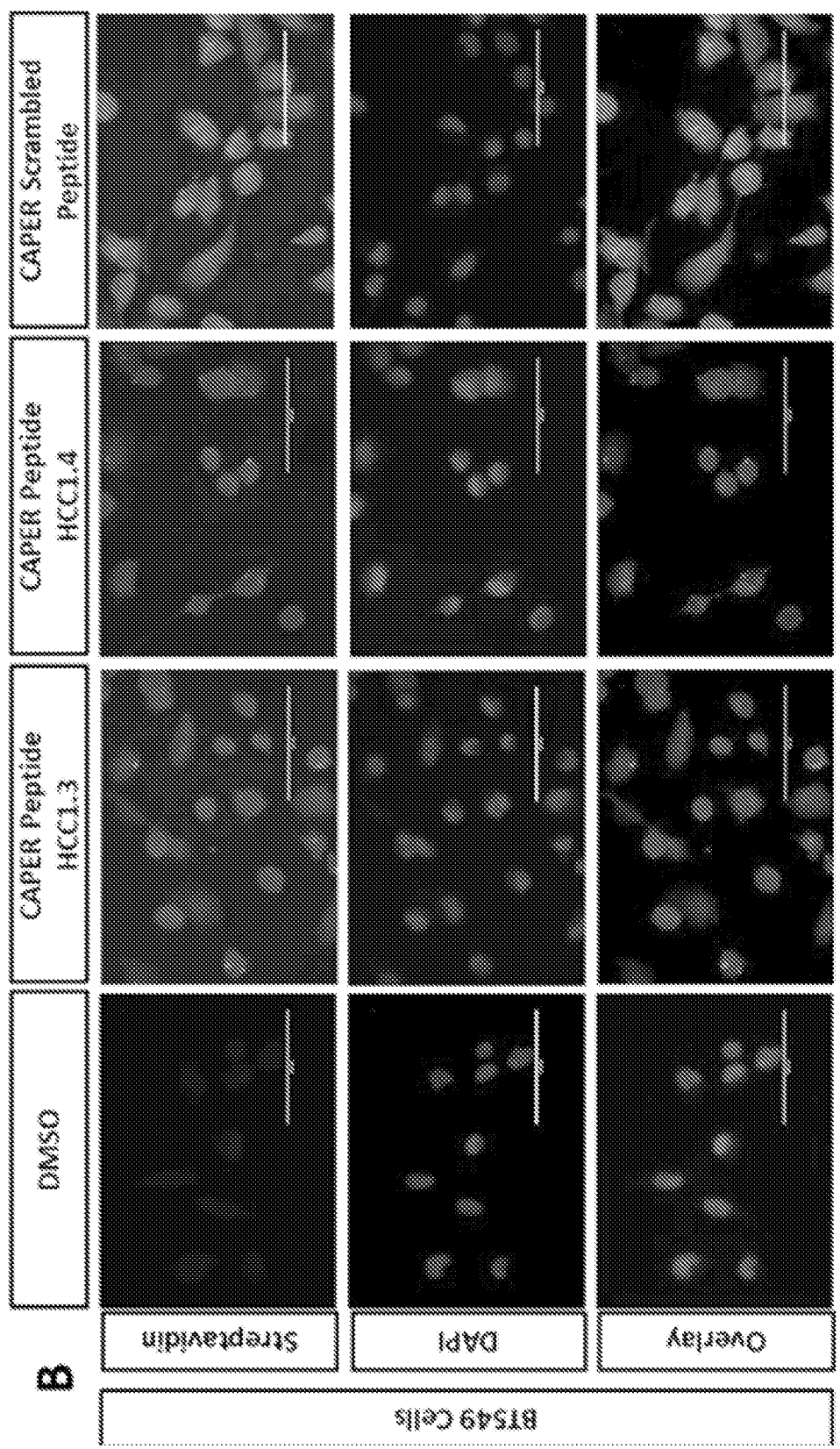
Figure 2C:
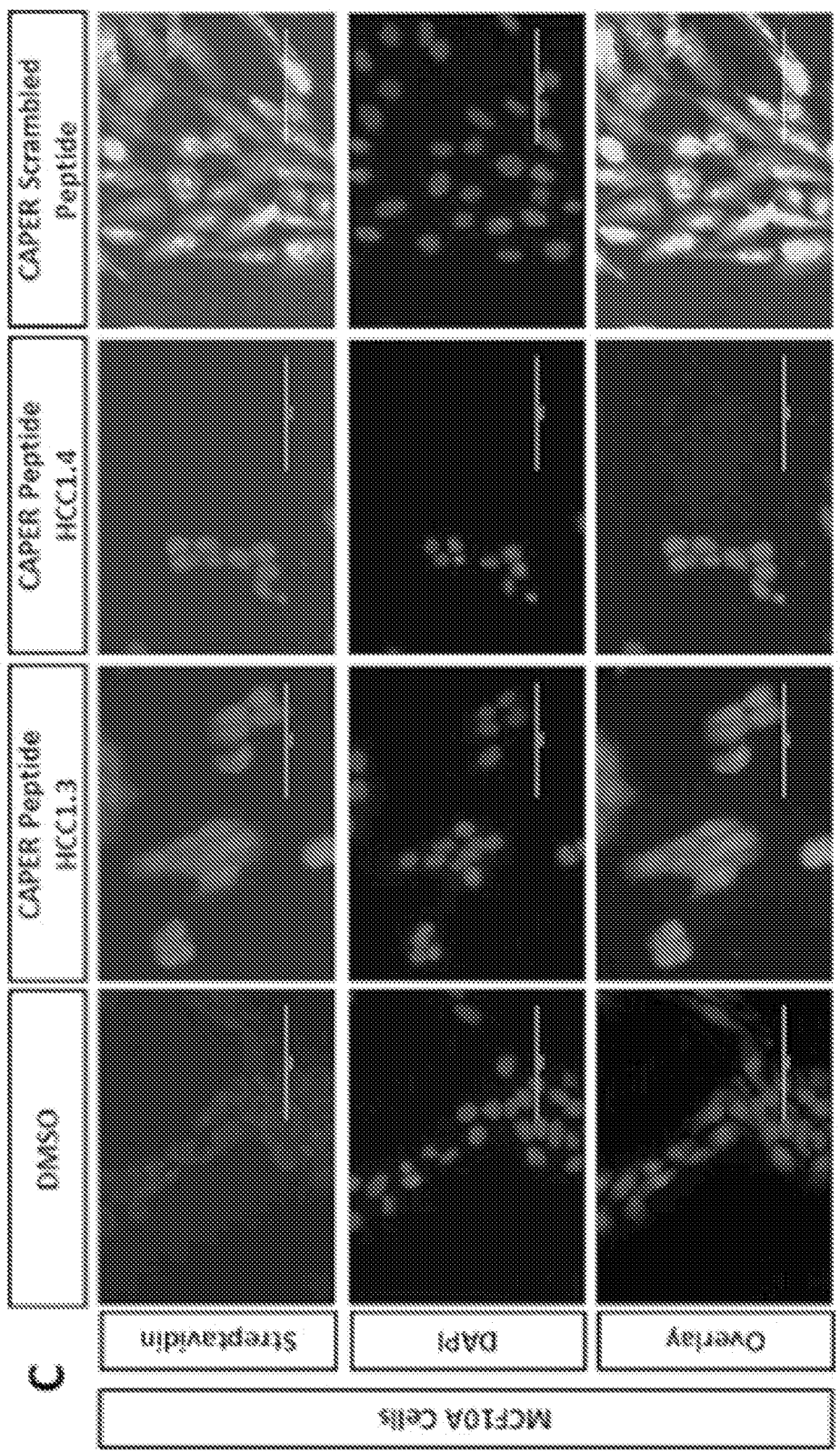
Figure 2D:
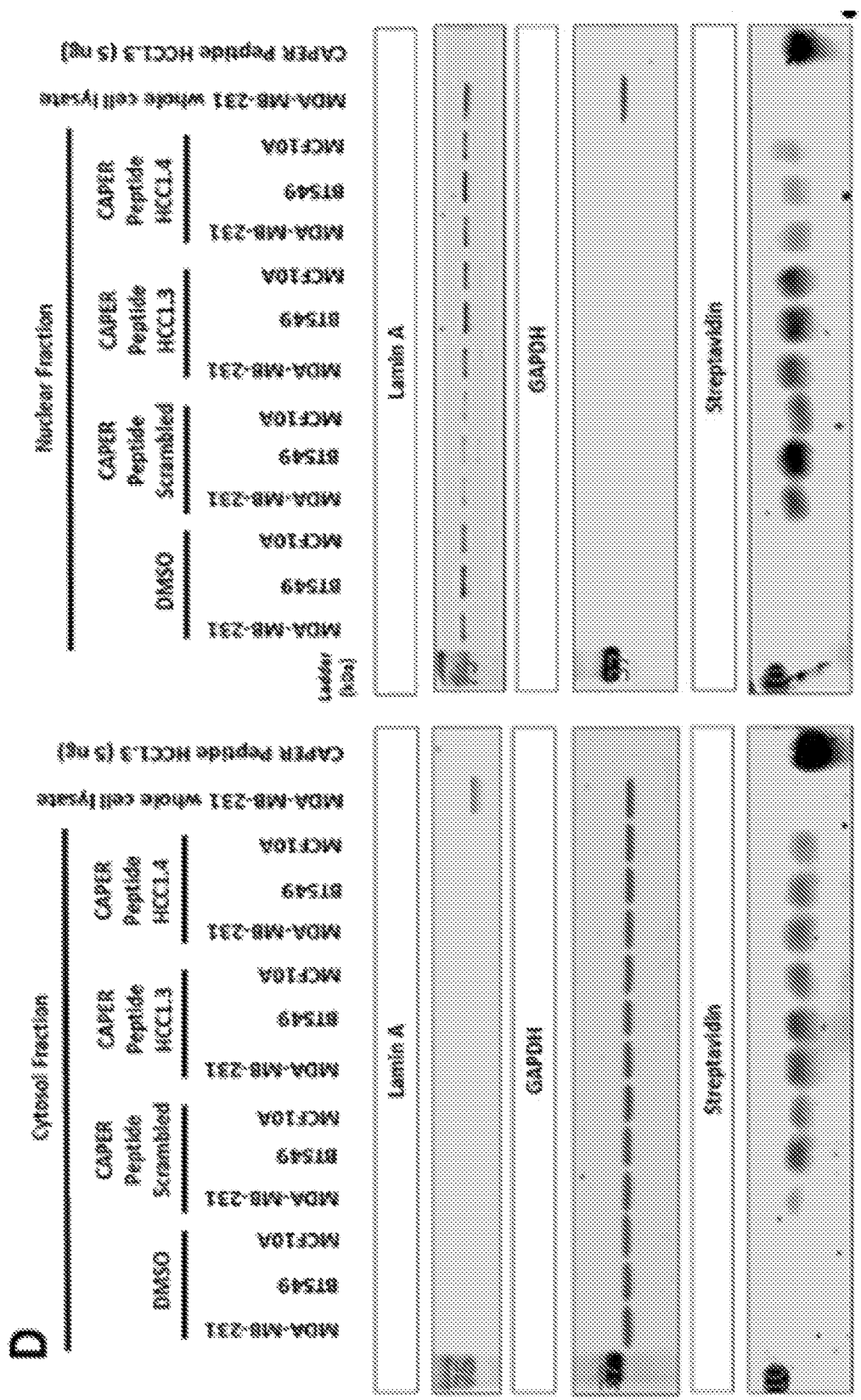

MDA-MB-231, BT549 and MCF10A cells were treated with 10 μM of CAPER peptide HCC1.3, CAPER peptide HCC1.4 and the CAPER peptide scrambled for 1 hr. Immunofluorescent staining of the cells show the peptides effectively enter the cells and travel to the nucleus after 1 hr of treatment (FIGS. 2A-2C). To confirm the results seen with immunofluorescence, fractionation was performed on the cell lines after treatment with the peptides to obtain cytosolic and nuclear proteins. Analysis of these lysates via Western blotting show similar results as the immunofluorescence staining, confirming that the peptides are entering the cells and traveling to the nucleus (FIG. 2D).

Figure 3A:
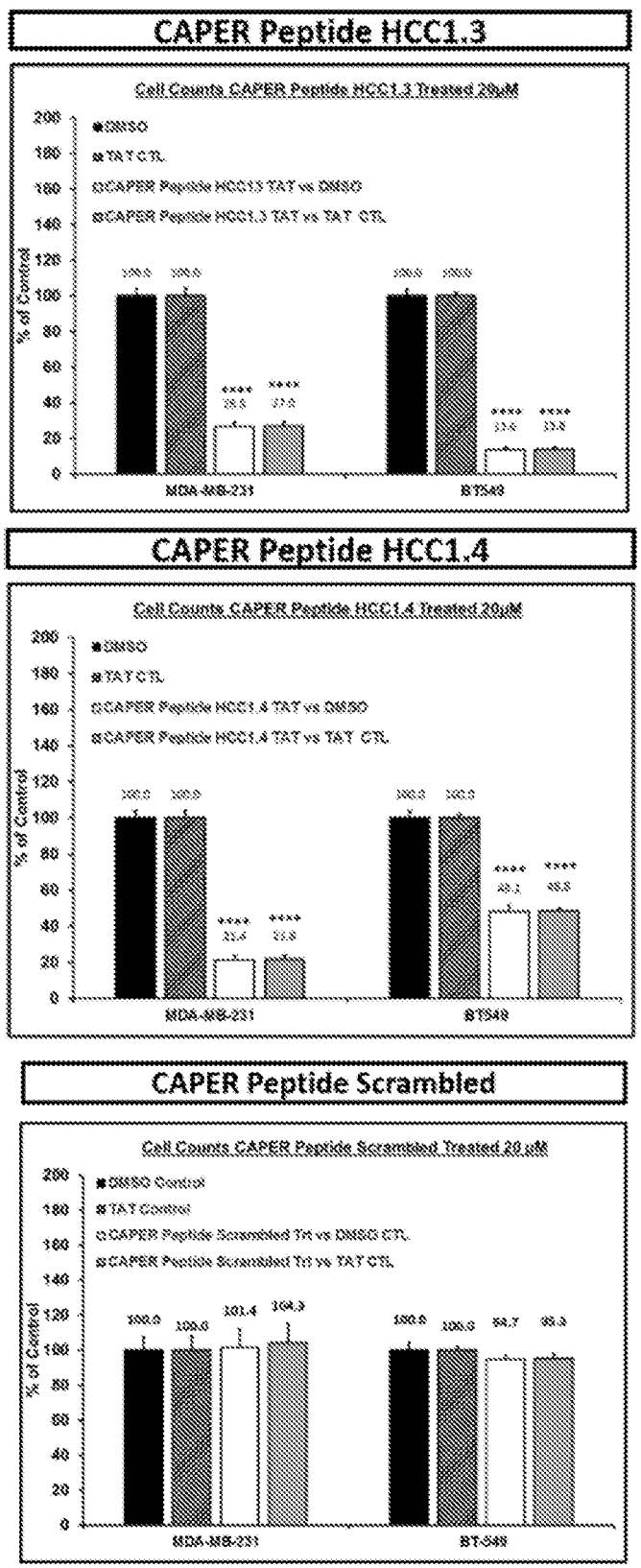
FIGS. 3A-3B are images showing that treatment of TNBC cell lines with CAPER peptides results in lower cell number.
Figure 3B:
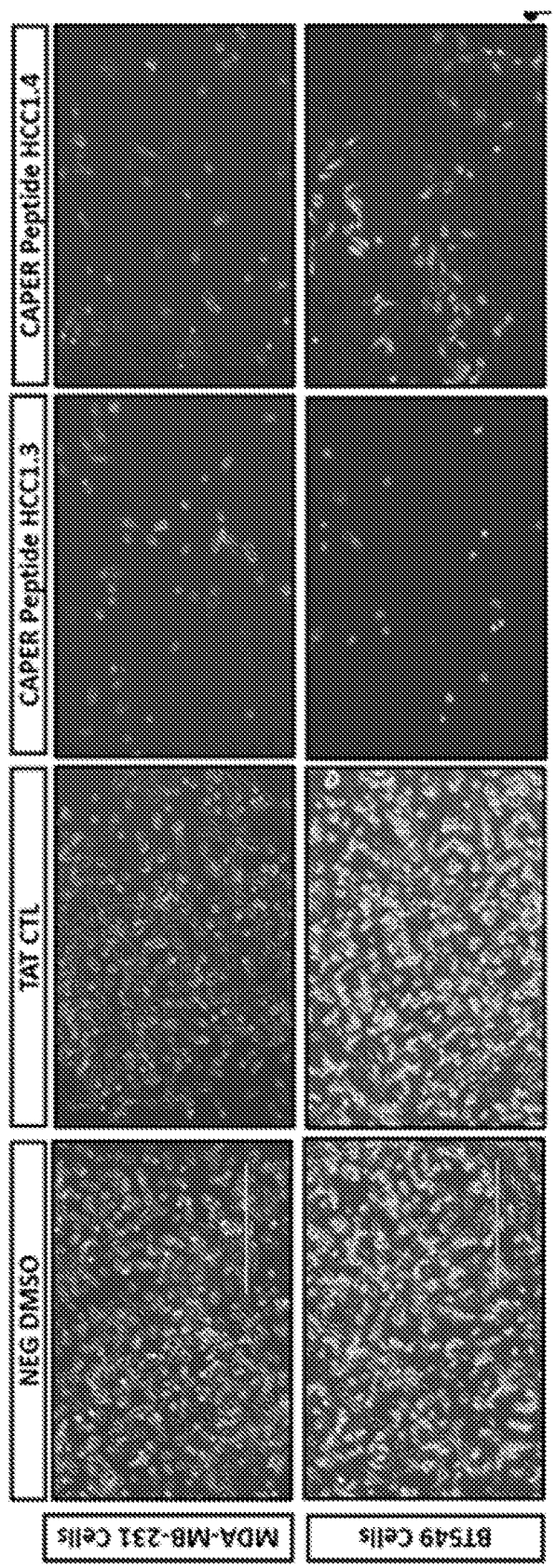
Figure 4A:
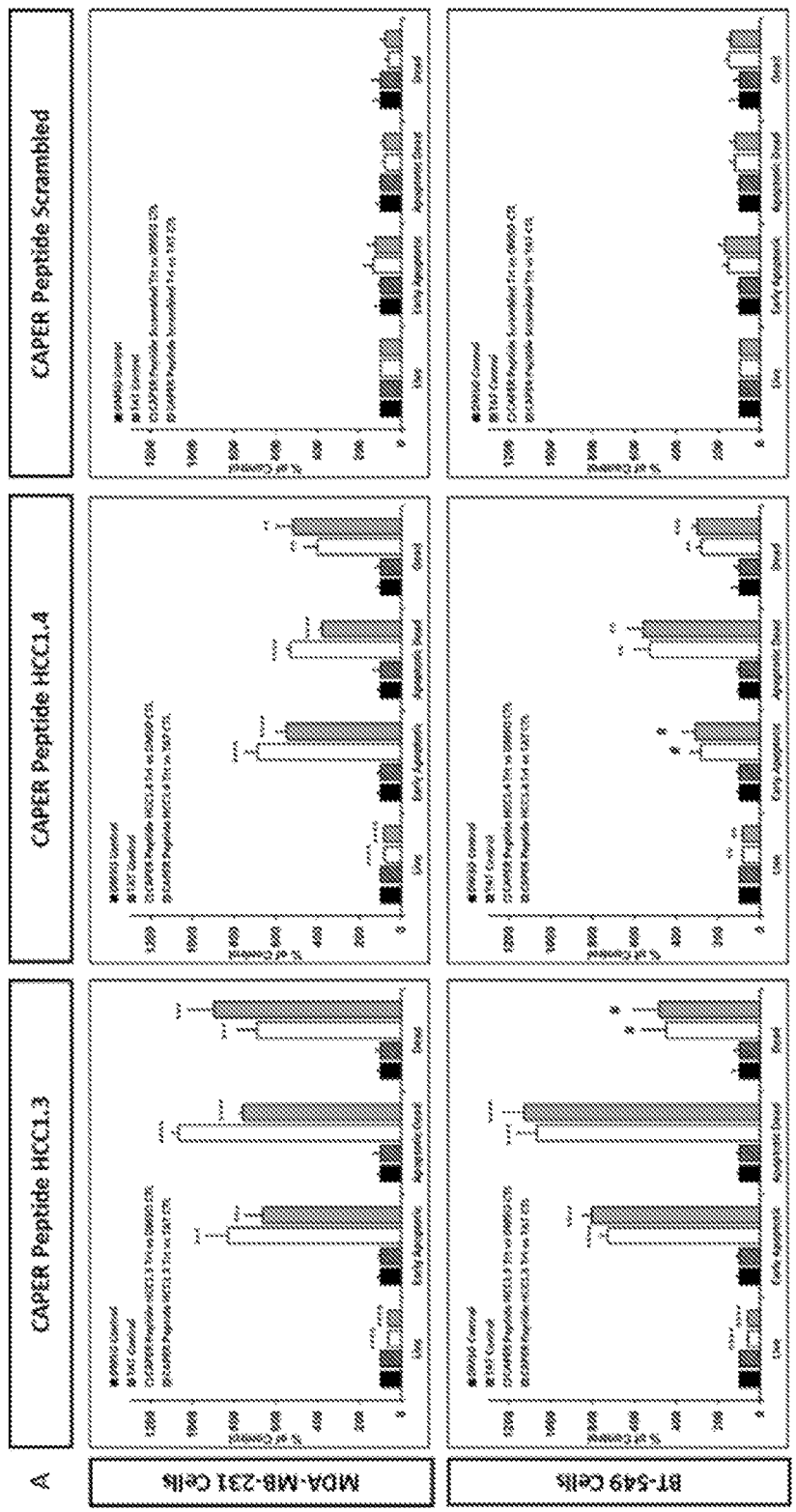
FIGS. 4A-4B illustrate that treatment of TNBC cell lines with CAPER peptides results in an increase in apoptosis.
Figure 4B:
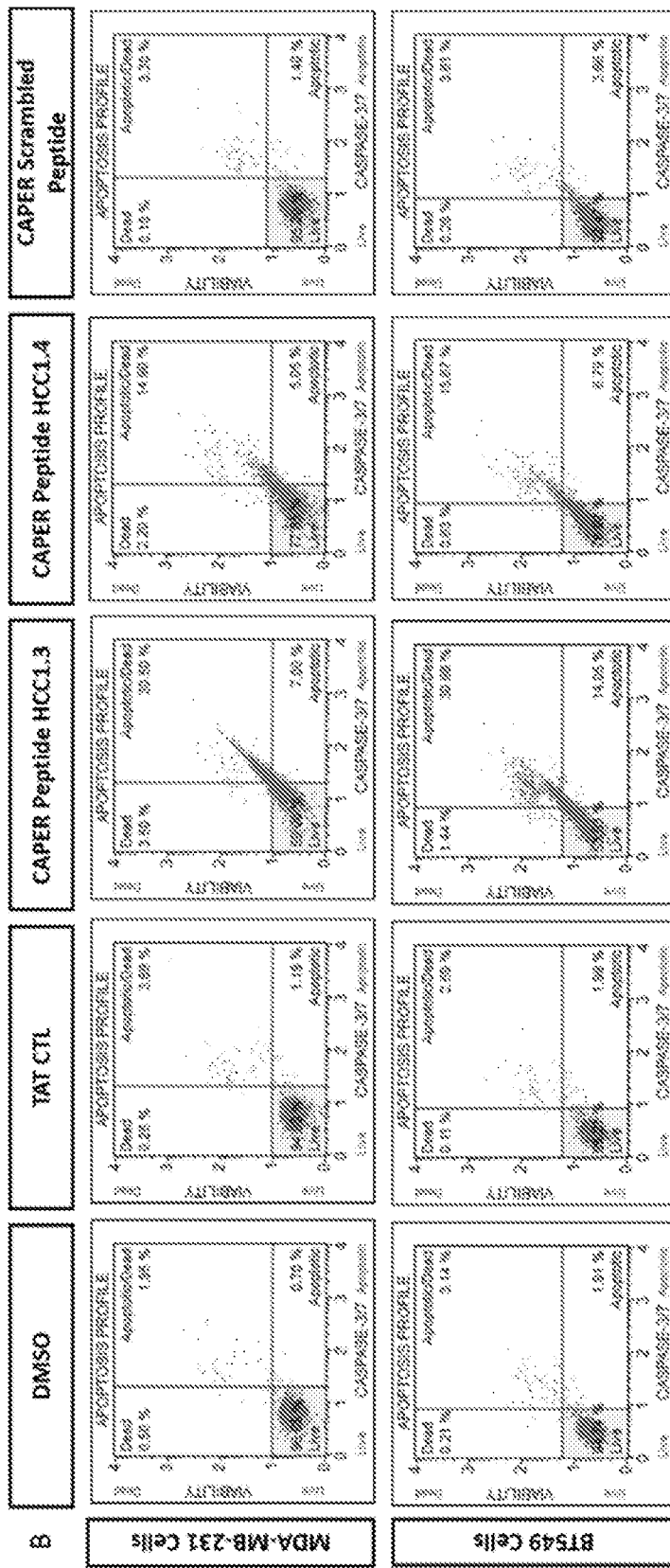
Figure 5A:
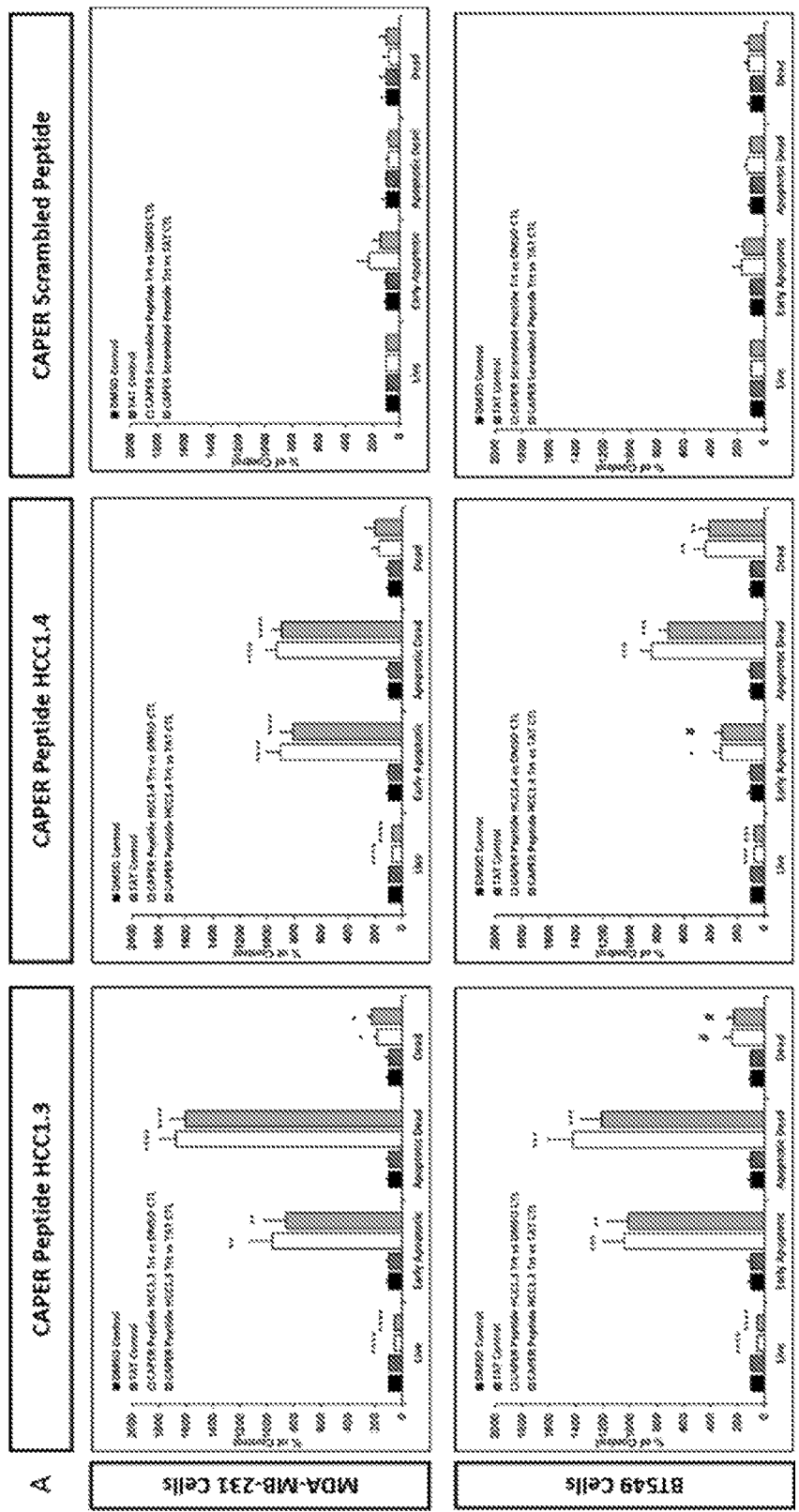
FIGS. 5A-5B illustrate that treatment of TNBC cell lines with CAPER peptides results in an increase in apoptosis.
Figure 5B:
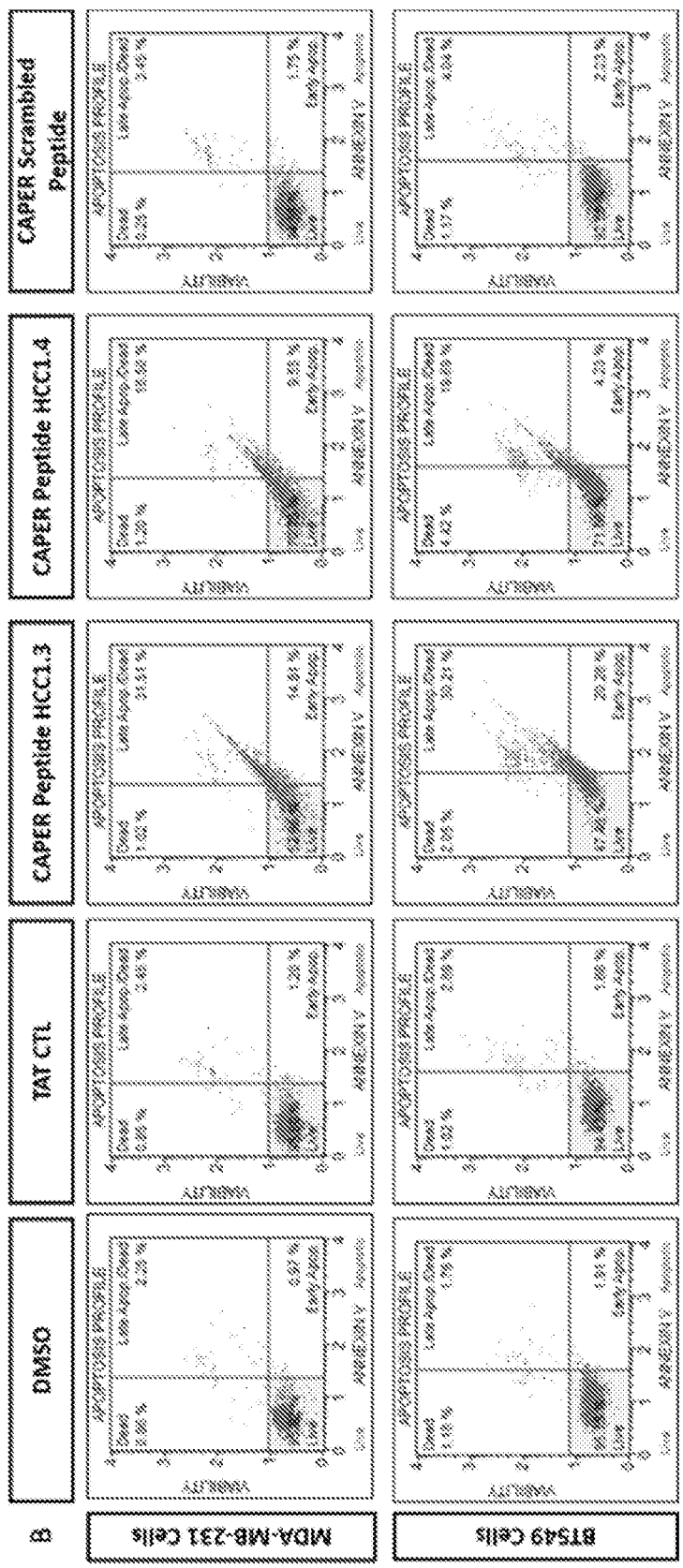
Figure 6A:
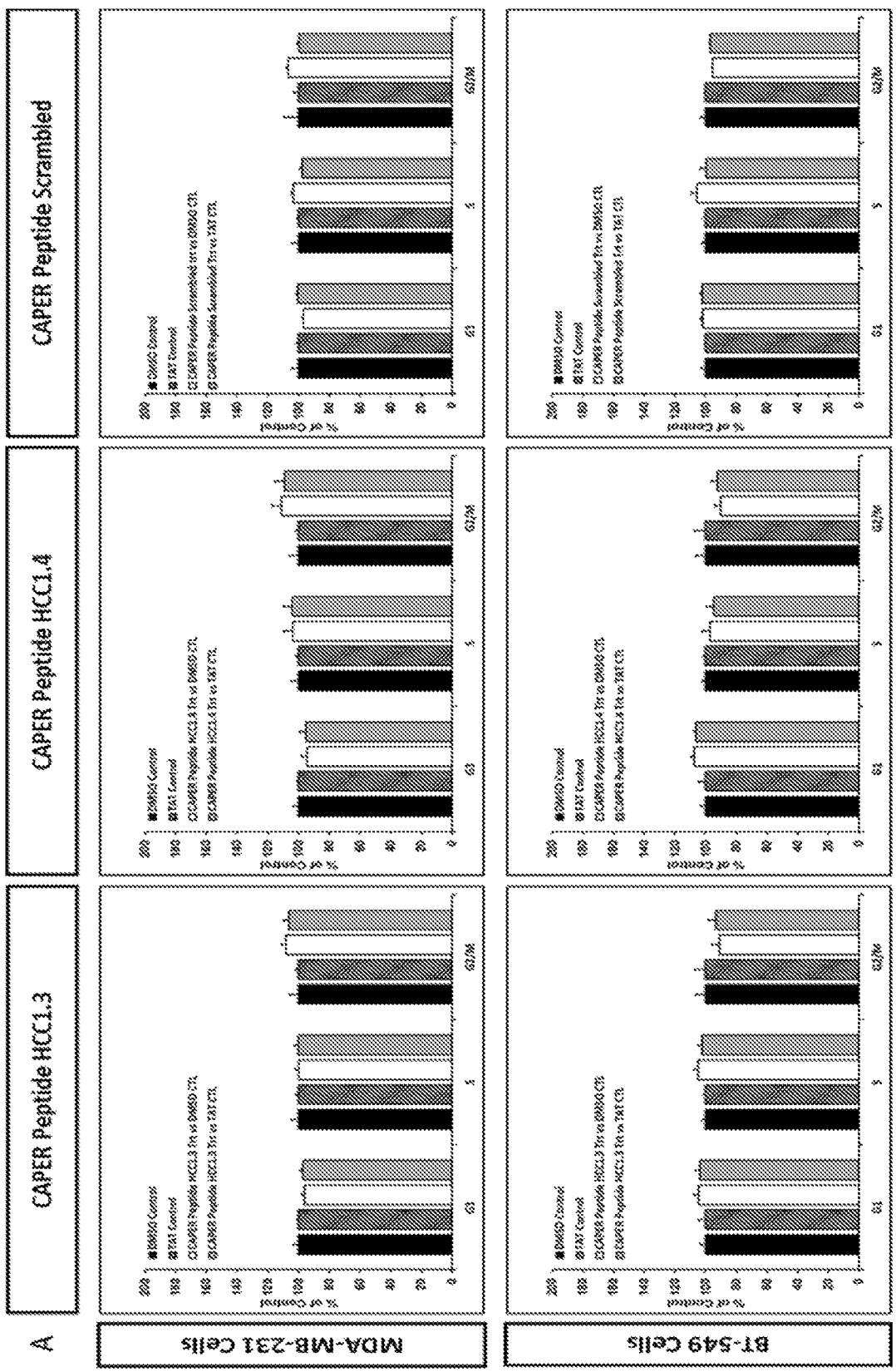
FIGS. 6A-6B illustrate that the treatment of nocodazole synchronized MDA-MB-231 and BT549 cells with CAPER peptides shows no effect on cell cycle.
Figure 6B:
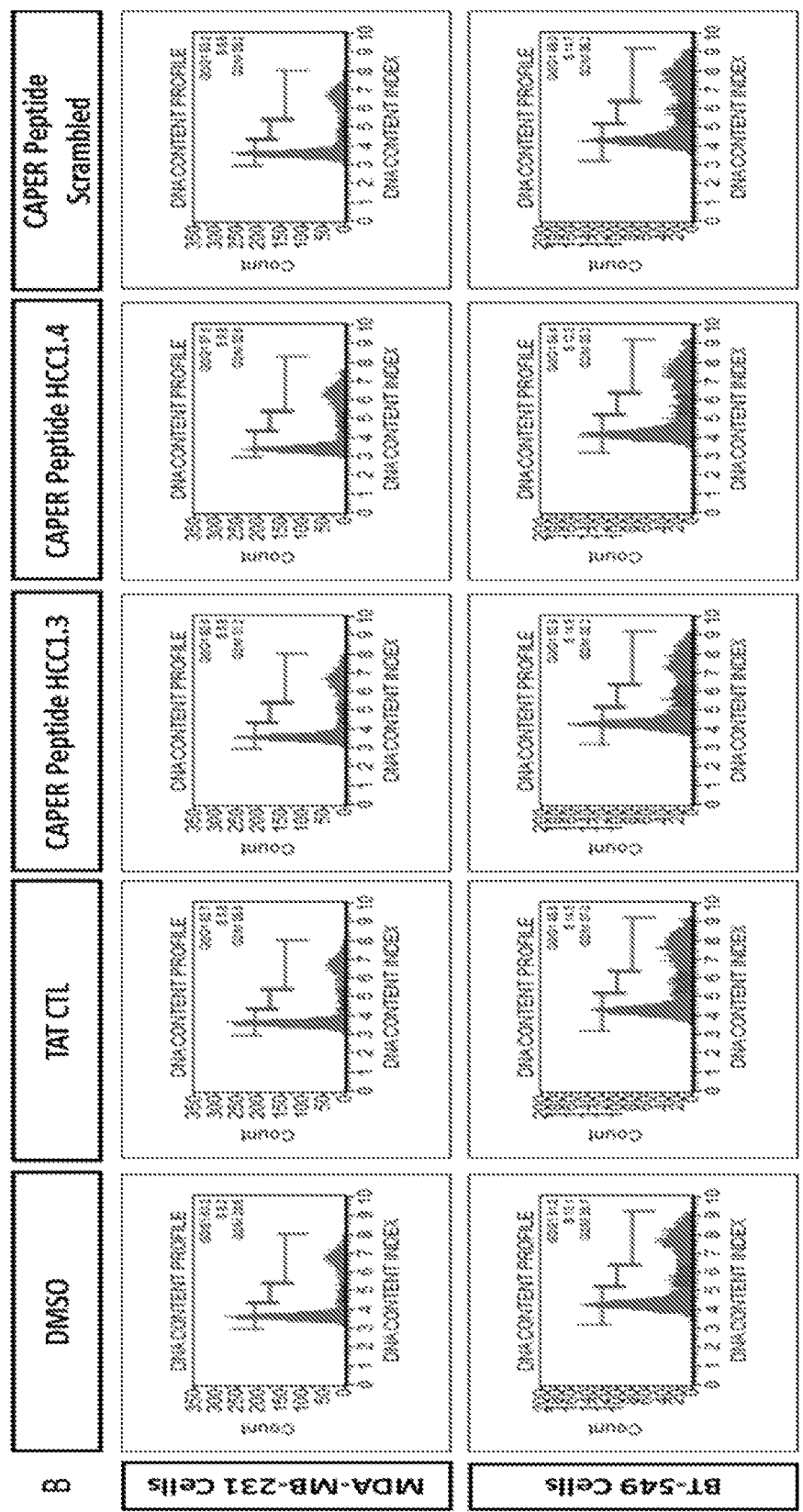

Example 3: Treatment of TNBC Cell Lines with CAPER Inhibiting Peptides Shows a Decrease in Cell Number and an Increase in Apoptotic Cells with No Effect on Cell Cycle After 7 days of treatment with either CAPER peptide HCC1.3 or CAPER peptide HCC1.4, both MDA-MB-231 and BT549 cells show a significant decrease in cell number (FIGS. 3A-3B). Additionally, when apoptotic cells were investigated, both TNBC cells lines treated with the peptides show a significant decrease in live cells and a significant increase in early apoptotic and apoptotic dead cells which is observed in both the Caspase 3/7 assay (FIGS. 4A-4B) as well at the Annexin-V assay (FIGS. 5A-5B). TNBC cells treated with the CAPER peptides show no effect on cell cycle (FIGS. 6A-6B).

Example 4: Treatment of TNBC Cell Line MDA-MB-231 with CAPER Peptides Decreases Phosphorylated c-Jun and Pro-Survival Protein Bcl-2 while Modulating Both AKT and NF-КB Pathways with No Effect on Cell Cycle Regulator Cyclin D1

Figure 7:
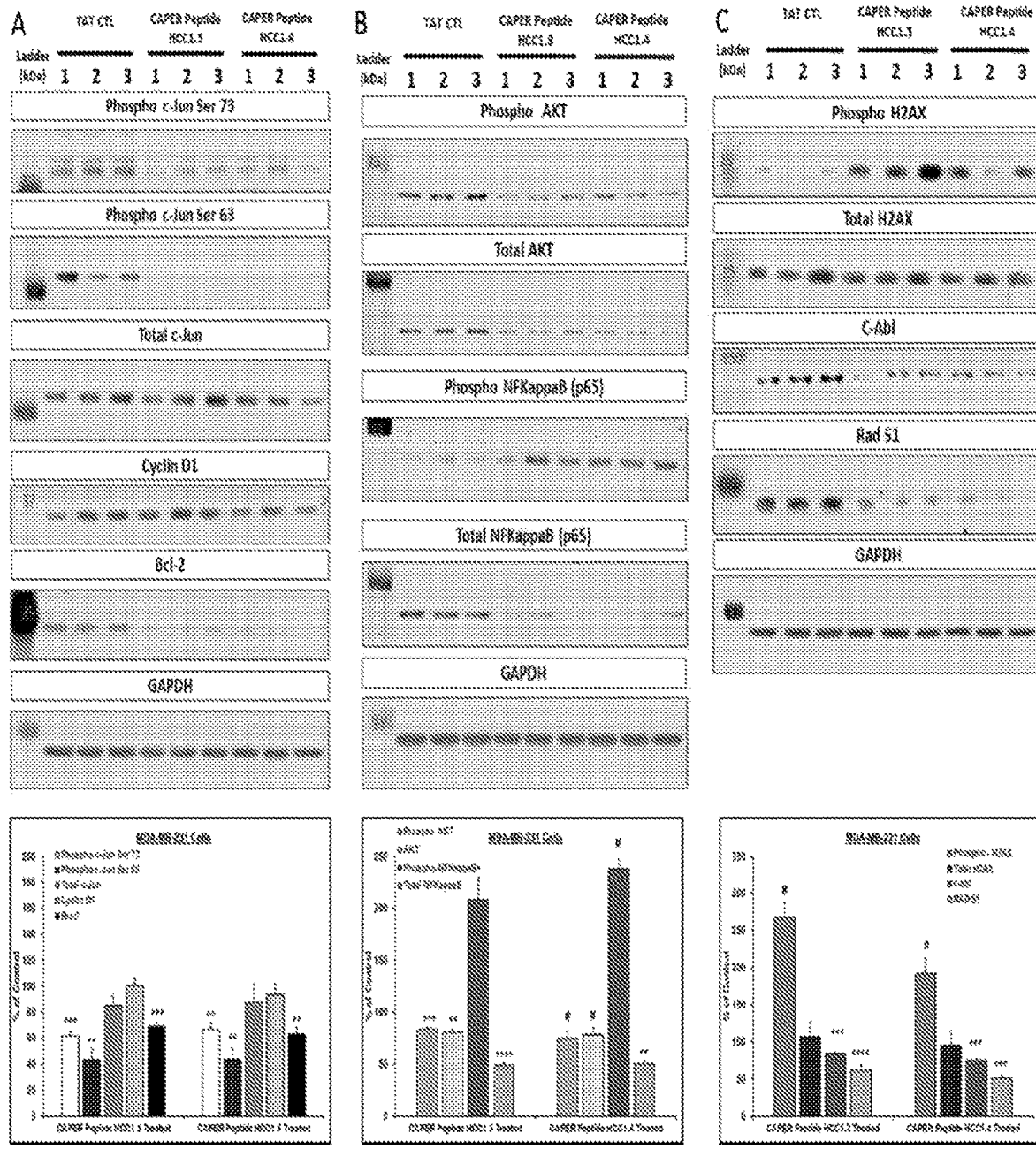
FIG. 7 shows Western blot analysis after treatment of TNBC cell lines with CAPER peptides. MDA-MB-231 cells treated with CAPER peptide HCC1.3 and HCC1.4 for 7 days. Each protein was divided by the GAPDH loading control and then normalized to TAT control treated which was normalized to 100%. Data represents the mean from three independent Western blots. **p<0.0001, *p<0.001, **p<0.005, *p<0.01, #p<0.05.

Since both CAPER peptides bind to c-Jun, and since c-Jun activation has been shown to be enhanced upon phosphorylation, total c-Jun and two phosphorylation events of c-Jun (Ser 73 and Ser 63) levels were investigated using Western blotting. The results shown in FIG. 7A illustrate that treatment with either peptide does not alter the level of total c-Jun but does decrease the levels of both c-Jun phosphorylation events. Levels of known pro-survival protein AKT, which is an upstream activator of c-Jun, were then investigated. Results show that peptide treatment results in both decreased levels of total and phosphorylated AKT (FIG. 7A). Since cross-talk occurs between c-Jun and NF-κB which can lead to cell survival via an inhibition of TNFα induced apoptosis, levels of total and phosphorylated NF-κB were ascertained. Interestingly, the results show a significant increase in phosphorylated NF-κB with a decrease in total NF-κB (FIG. 7B), both of which are seen during TNFα induced apoptosis. Additionally, the level of pro-survival protein Bcl-2, which can be regulated by AKT, c-Jun, and NF-κB were investigated and results show a significant decrease after peptide treatment (FIG. 7A), indicating a shift towards the pro-apoptotic state. Since c-Jun can affect cell cycle progression primarily through the regulation of cyclin D1, we investigated these levels which shows no significant change confirming the results seen in the cell cycle assay (FIG. 7A).

Example 5: Treatment of TNBC Cell Line MDA-MB-231 with CAPER Peptides Induces Phosphorylation of Histone H2AX while Decreasing Proteins Involved in DNA Repair Knockdown of CAPER causes activation of DNA damage markers and a decrease in DNA repair proteins. To see if the CAPER peptides had a similar effect, the levels of phospho-H2AX (γ-H2AX), RAD51 and c-abl were investigated. The results shown in FIG. 7C show an increase in phospho-H2AX (γ-H2AX) indicating DNA damage, and a decrease in proteins involved in DNA repair (RAD51, c-abl). All of these data implicate CAPER as an important regulator of DNA repair pathways.

Figure 8:
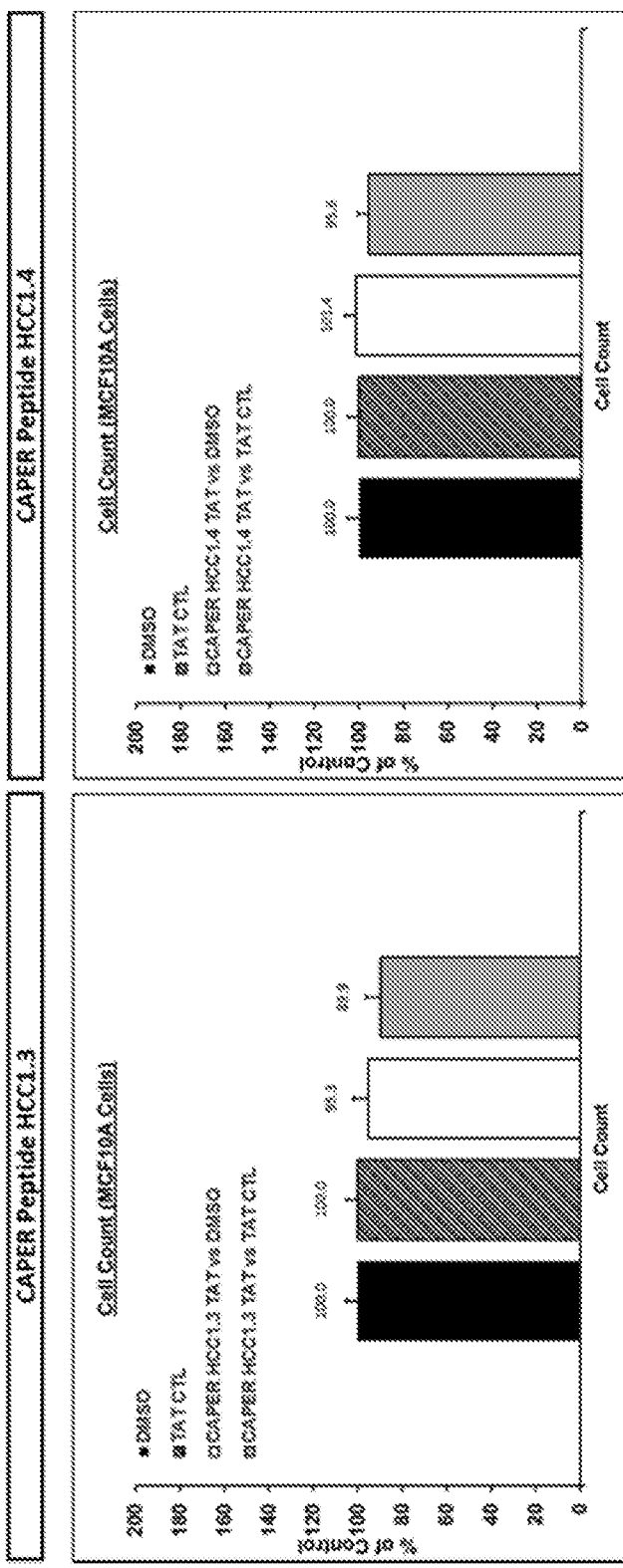
FIG. 8 show graphs illustrating that the treatment of non-tumorigenic cell line MCF10A shows no change in cell count with treatment of CAPER peptides. Cell counts for MCF10A cells treated for 7 days with 20 µM of CAPER peptide HCC1.3 and CAPER peptide HCC1.4 compared to DMSO and TAT treated controls, p=not significant, n=3.
Figure 9A:
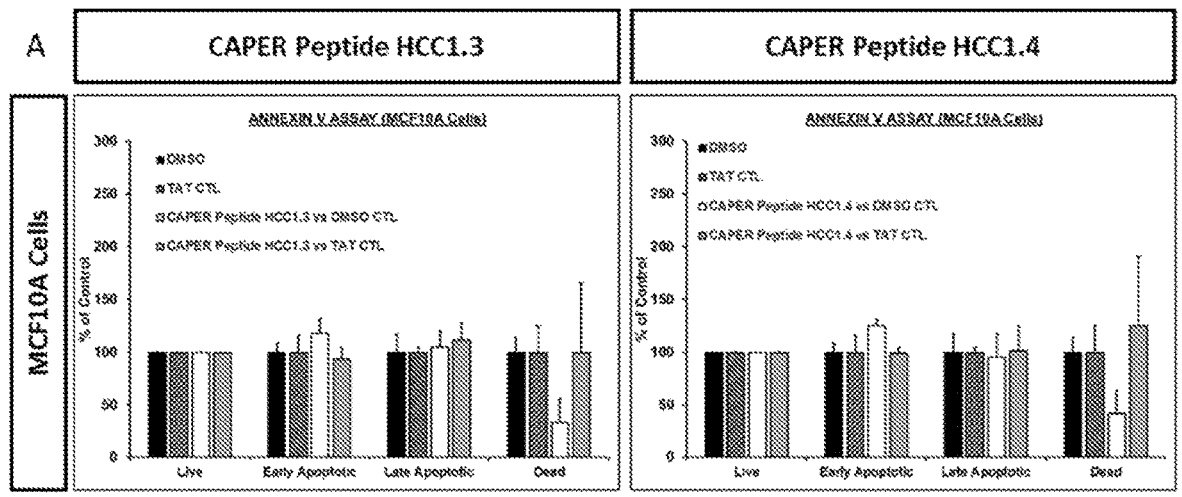
FIGS. 9A-9B illustrate that treatment of normal breast epithelial cell line MCF10A with CAPER peptides results in no change in apoptosis.
Figure 9B:
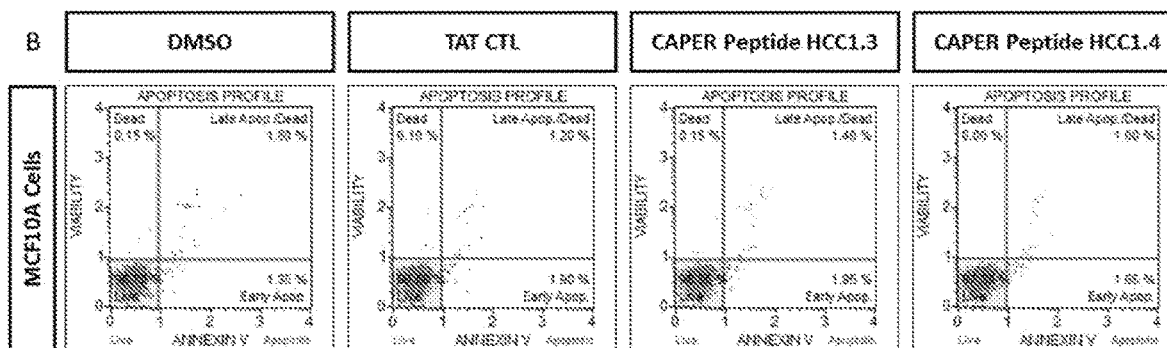
Figure 10A:
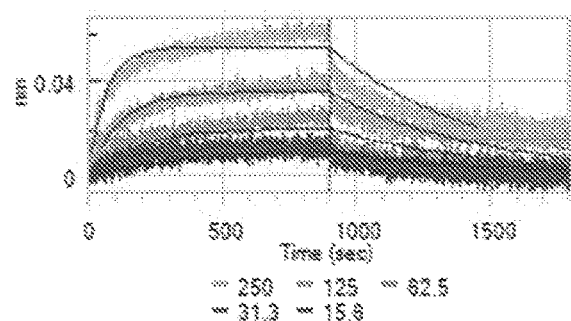
FIGS. 10A-10C show that CAPER peptides HCC1.3 and HCC1.4 bind to ERα with nM affinity and alter the binding of full-length recombinant CAPER.
Figure 10A:
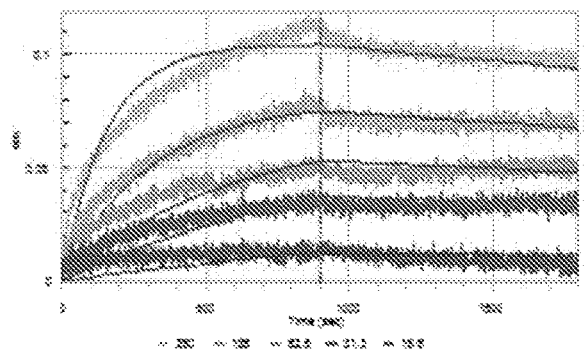
Figure 10A:
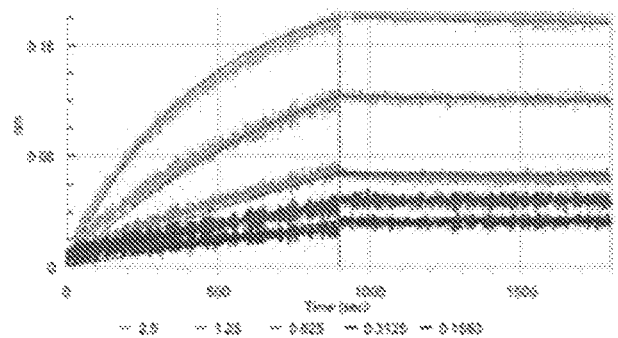
Figure 10A:
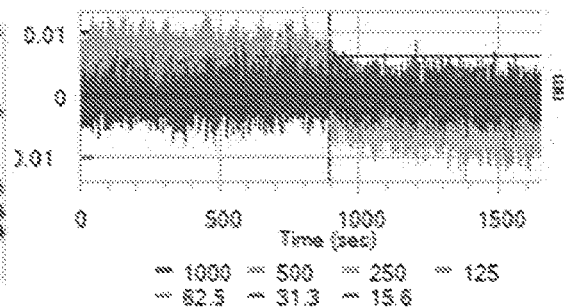
Figure 10A:
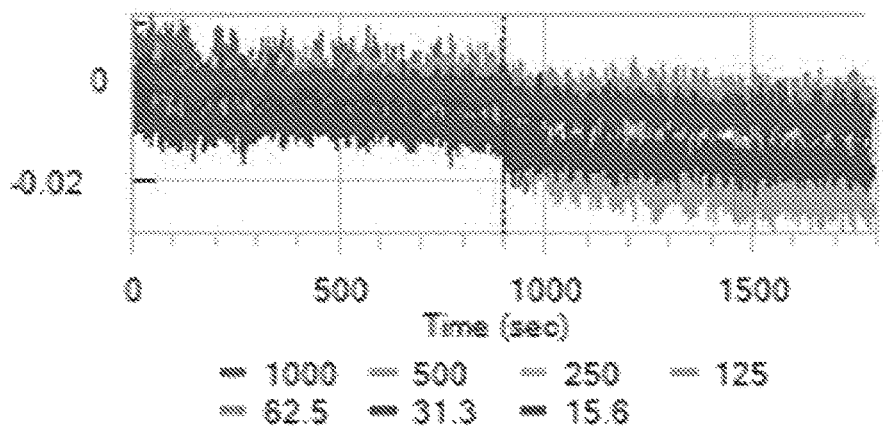
Figure 10B:
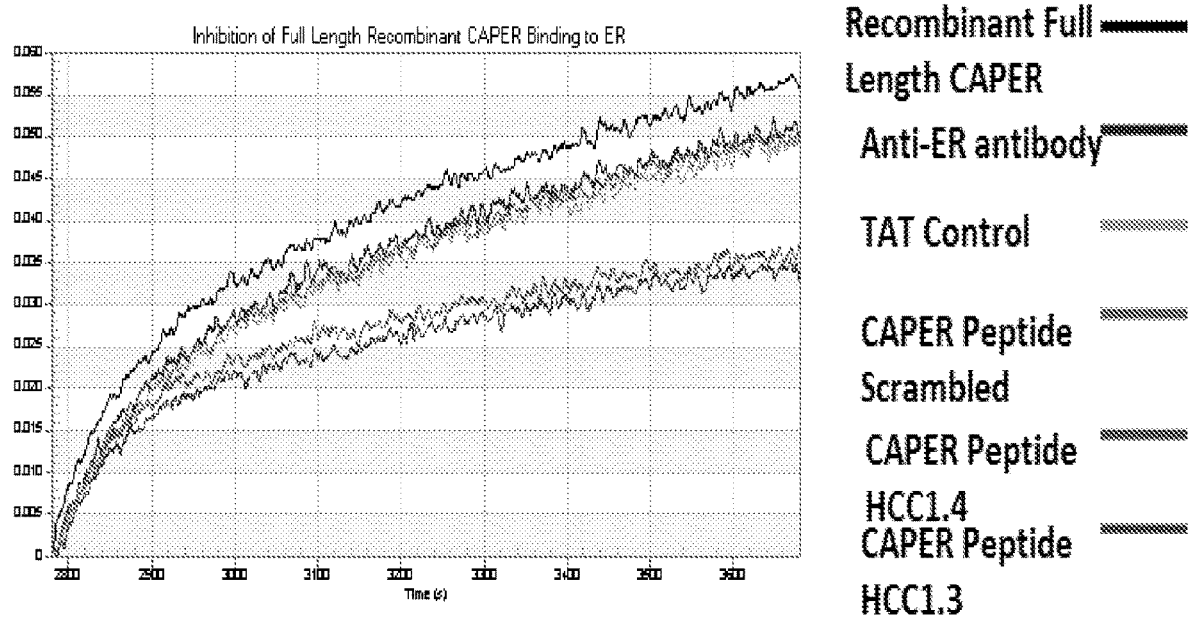
Figure 10C:
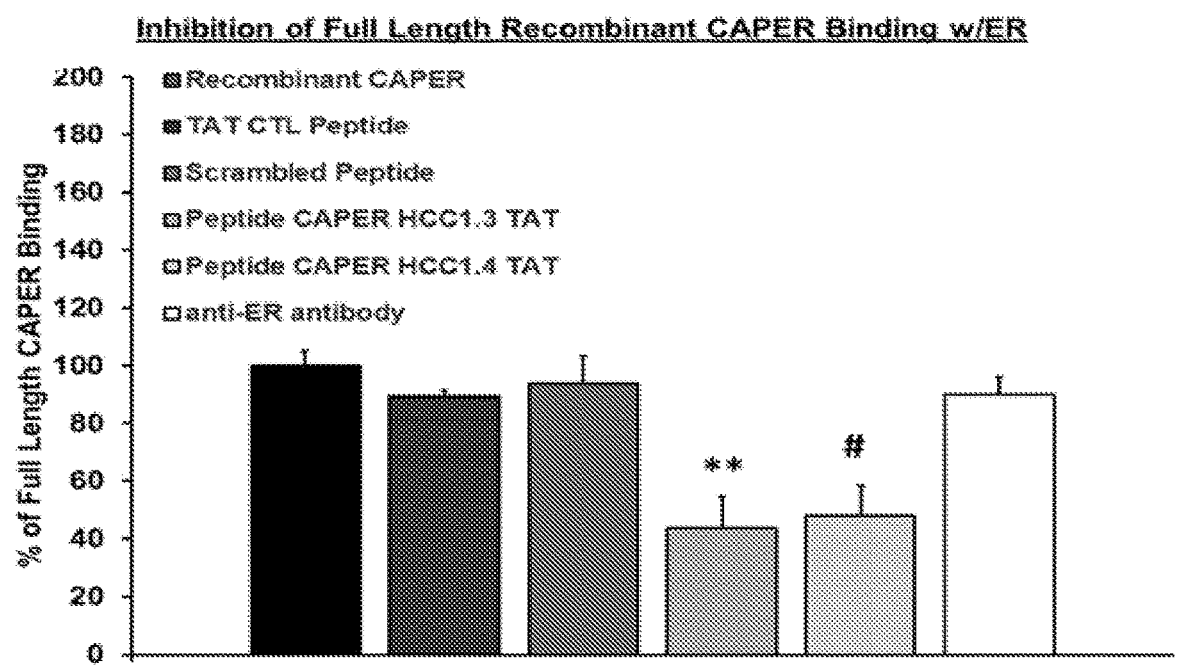

Example 6: Treatment of Non-Tumorigenic Cell Line MCF10A with CAPER Inhibiting Peptides Results in No Effect on Cell Number or Apoptosis Normal non-tumorigenic breast epithelial cell line MCF10A was treated with either CAPER peptide HCC1.3 or CAPER peptide HCC1.4 for 7 days. After the 7 day treatment period, the MCF10A cell line showed no significant change in cell count (FIG. 8) or apoptotic cells when compared to both DMSO and TAT controls (FIGS. 9A-9B).

Example 7: CAPER Peptides Bind to ERα with nM Affinity and Alter Binding of Recombinant Full-Length CAPER with ERα (Table 2)

TABLE 2

Binding to Estrogen Receptor α

| | KD (nM) | K on (1/Ms) | K off (1/s) | X^2 | R^2 |
|---|---|---|---|---|---|
| CAPER Peptide HCC1.4 | 30.18 | 5.71E+04 | 1.72E−03 | 0.064 | 0.9297 |
| CAPER Peptide HCC1.3 | 4.50 | 2.54E+04 | 1.15E−04 | 0.0892 | 0.9737 |
| Recombinant Full-Length CAPER HCC1.3 | 0.02 | 9.37E+05 | 2.34E−05 | 0.0843 | 0.9917 |
| CAPER Scrambled Peptide | N.D. | | | | |
| TAT Control Peptide | N.D. | | | | |

Figure 11:
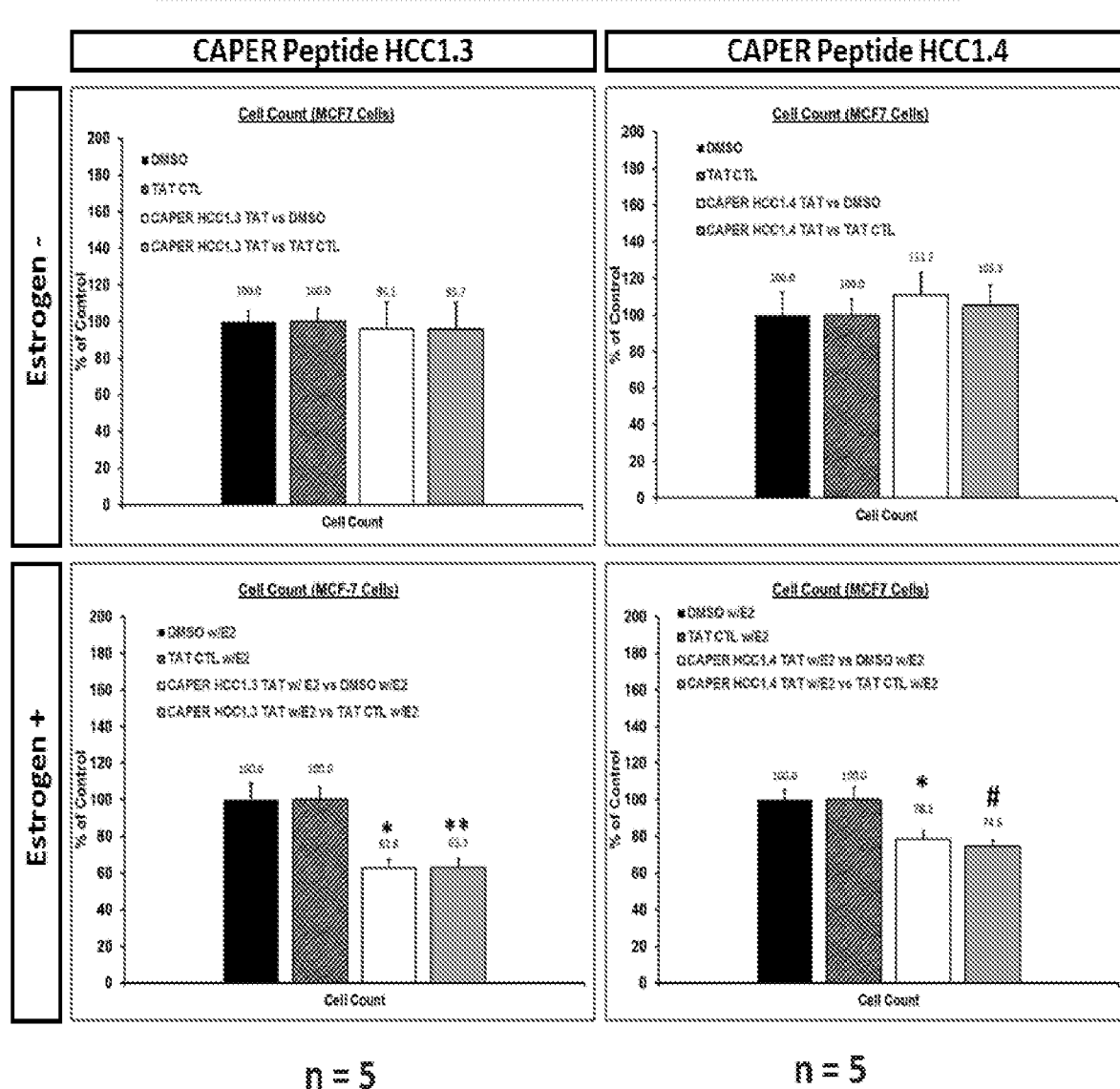
FIG. 11 shows graphs for cell counts for MCF7 cells treated with 20 µM of CAPER peptide HCC1.3, CAPER peptide HCC1.4 to DMSO and TAT controls.
Figure 12A:
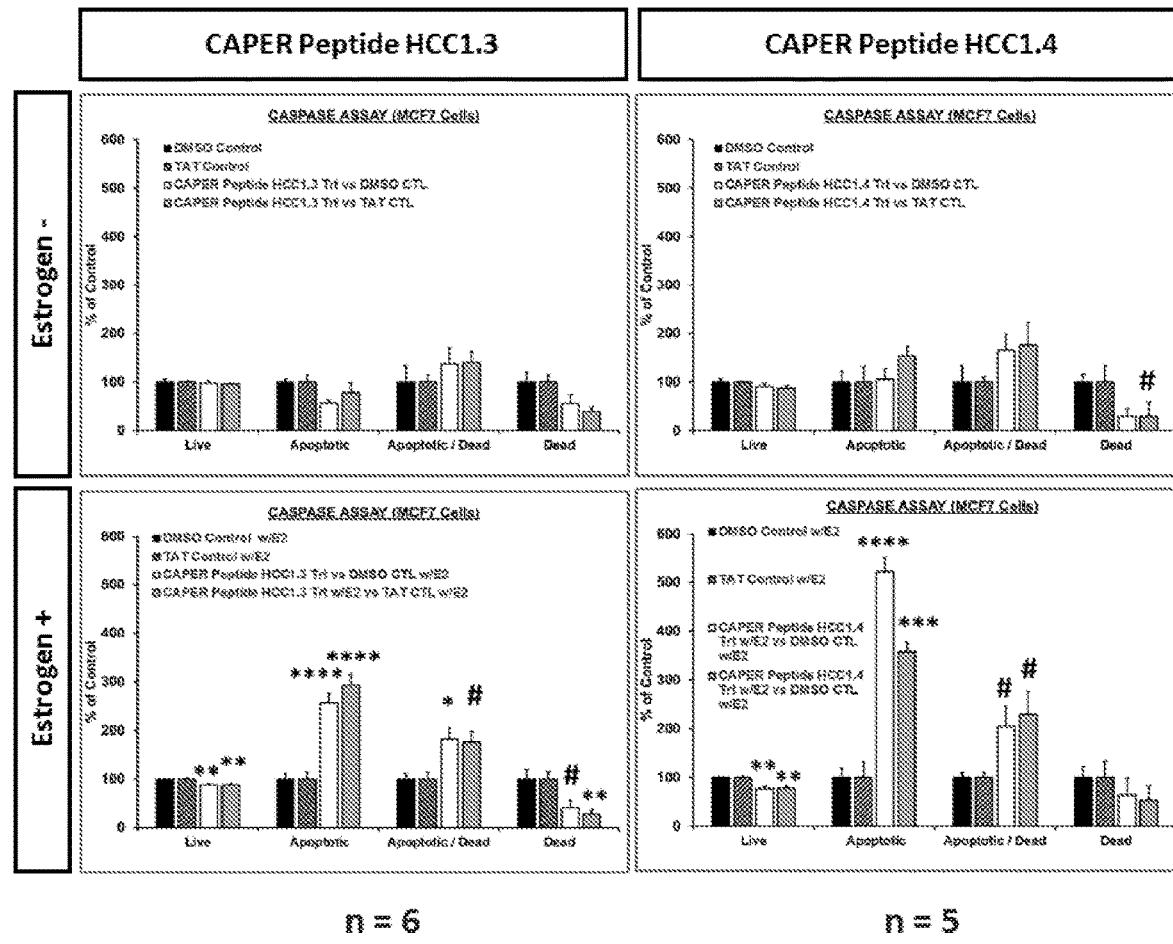
FIGS. 12A-12B are graphs showing results from Caspase 3/7 assay.
Figure 12B:
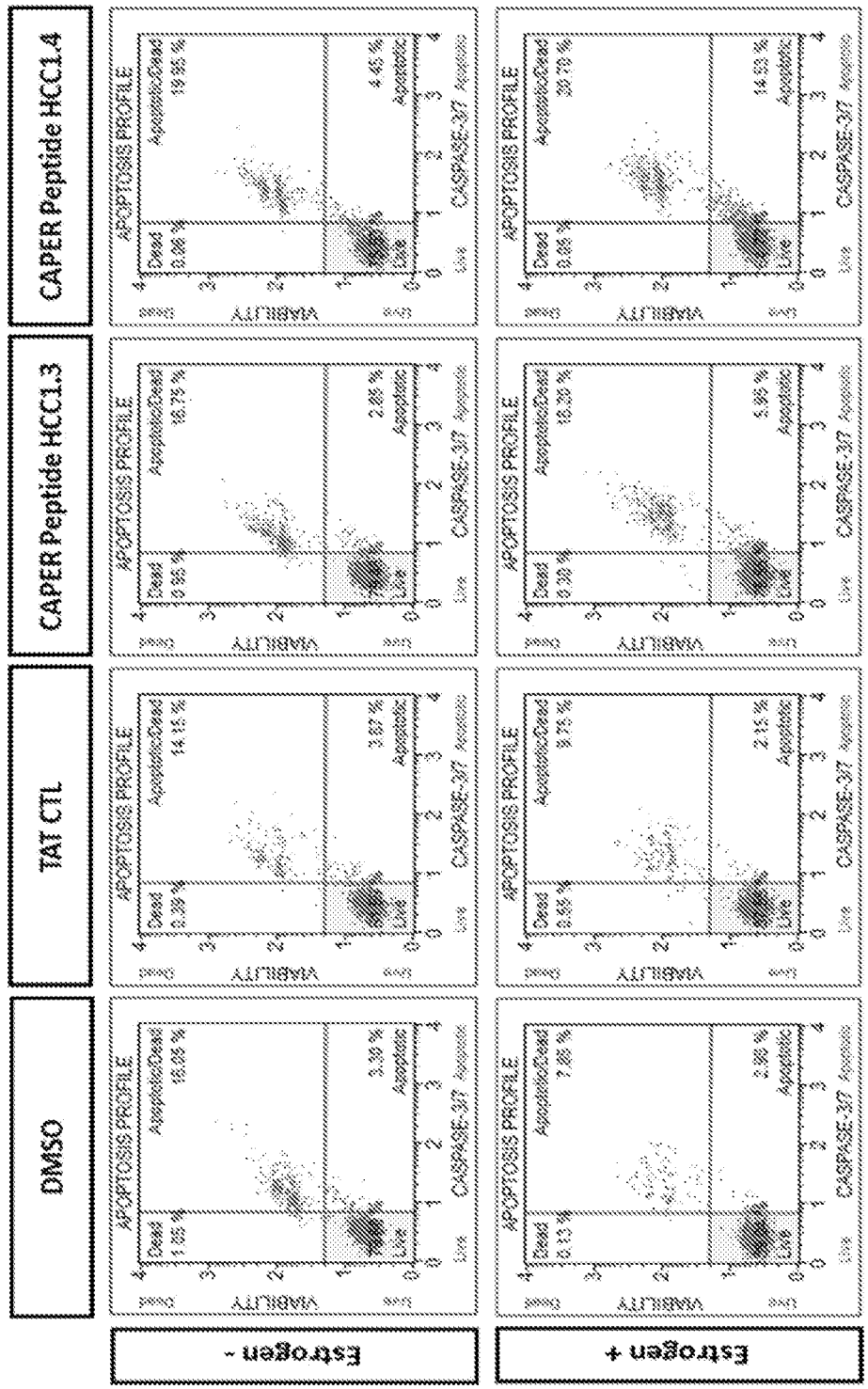
Figure 13A:
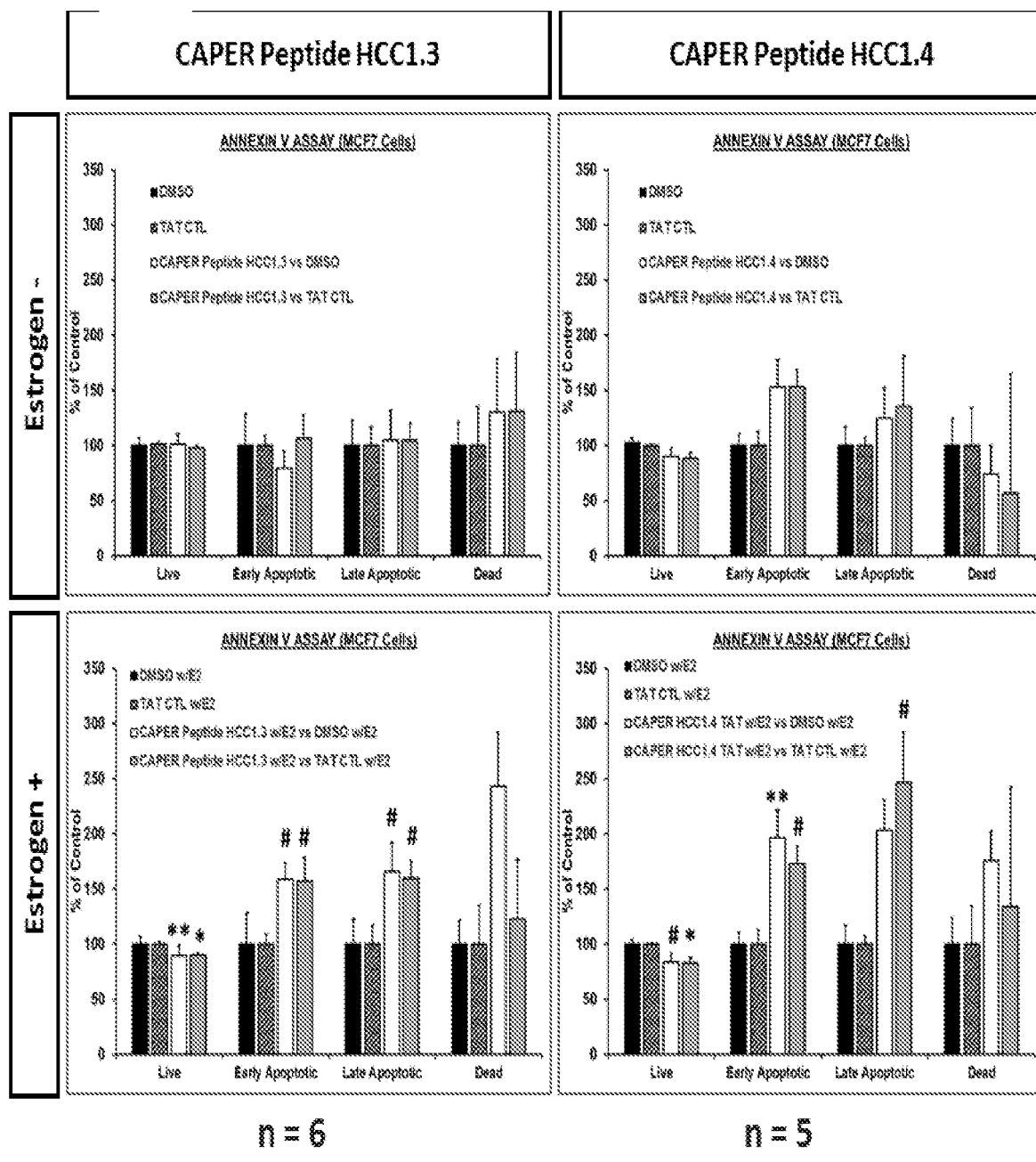
FIGS. 13A-13B show results from the Annexin V assay.
Figure 13B:
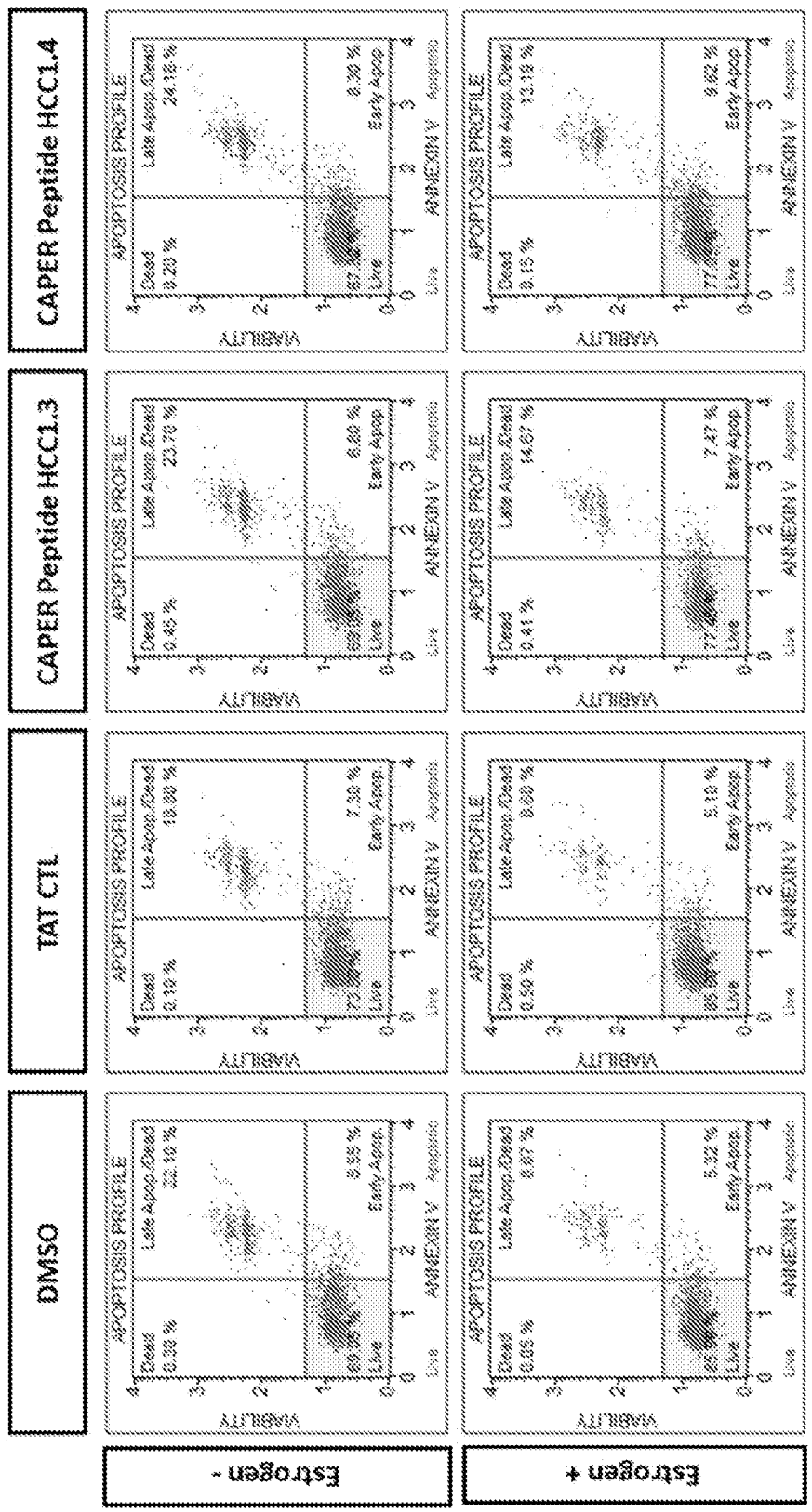

Example 8: MCF7 Cells Treated with CAPER Peptides Result in Lower Cell Number and an Increase in Apoptosis in the Presence of Estrogen MCF7 cells were serum starved and then treated for 7 days with either CAPER peptide HCC1.3 or CAPER peptide HCC1.4 with and without estrogen. Results show a significant decrease in cell number in the presence of estrogen when the cells are treated with the CAPER peptides (FIG. 11). Additionally, when apoptotic cells were investigated, MCF7 cells treated with the peptides in the presence of estrogen show a significant decrease in live cells and a significant increase in early apoptotic and apoptotic dead cells which is observed in both the Caspase 3/7 assay (FIGS. 12A-12B) as well as the Annexin-V assay (FIGS. 13A-13B).

Example 9: Effect of CAPER-Derived Cell Permeable Peptides on Brain Cancer

Figure 14:
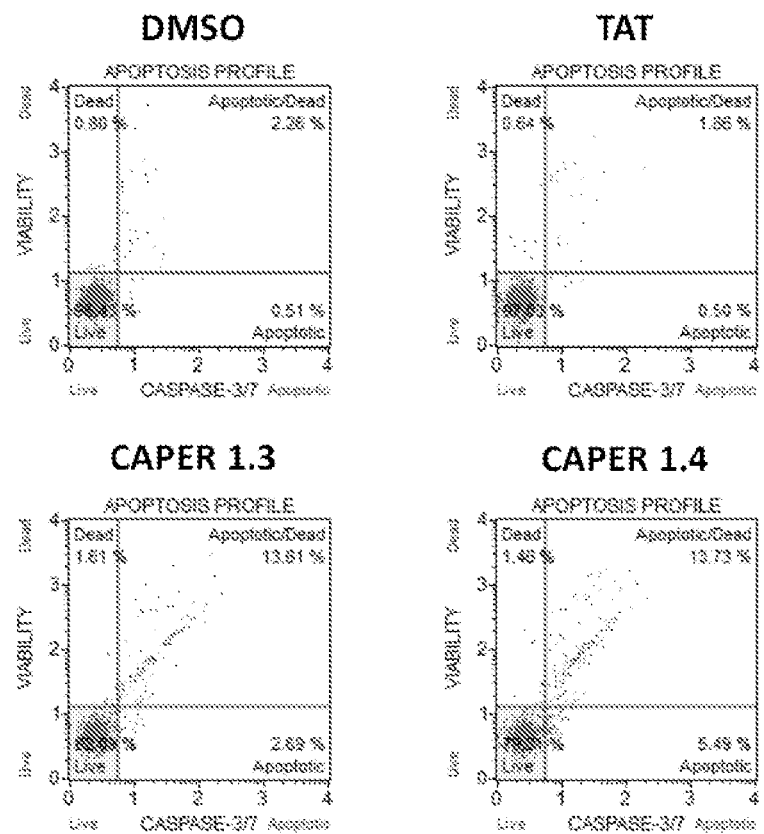
FIG. 14 shows that the treatment of human brain cancer cells (U-87MG) with 15 µM of CAPER peptides led to a reduction in survival and an increase in apoptosis of the cells.
Figure 14:
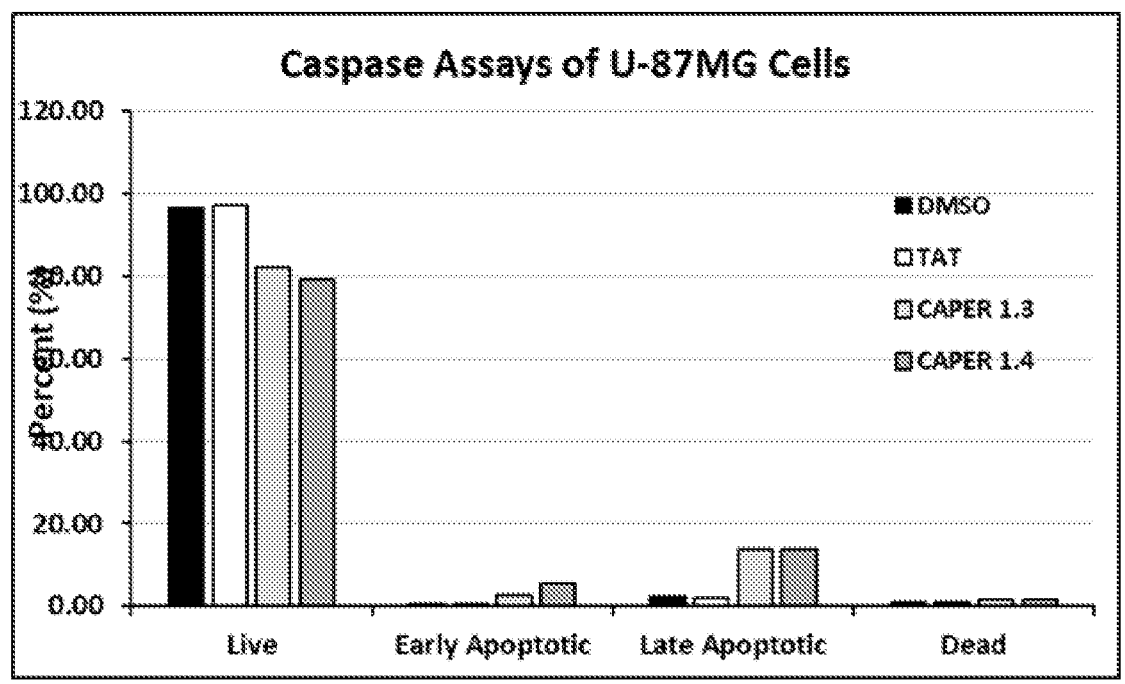

When the brain cancer cells (U-87MG) are treated with 15 μM of CAPER derived peptides, a reduction in survival and an increase in apoptosis was observed (FIG. 14).

Example 10

There are limited therapies currently available for patients with TNBC and so additional therapy options are urgently needed. Targeting CAPER activity with CAPER derived peptides can provide therapeutic benefit to patients suffering from TNBC. The data presented herein demonstrate for the first time the in vitro effect upon treating TNBC cell lines with CAPER peptides.

The data herein shows good binding affinity of the CAPER peptides to c-Jun in the nM range. Additionally, treatment of TNBC MDA-MB-231 and BT549 cell lines with either of the CAPER peptides results in a decrease in cell number and an increase in apoptotic cells. Without wishing to be limited by any theory, competition experiments show a potential mechanism of action of these peptides can be caused by the inhibition of CAPER's endogenous co-activator activities. In certain embodiments, the peptides are responsible for these pro-apoptotic effects. In other embodiments, the CAPER peptides bind to c-Jun and inhibit or alter the binding of endogenous CAPER thus modifying its co-activator activity and/or pre-mRNA splicing function. The data from competition experiments support this hypothesis. In yet other embodiments, the peptides inhibit other co-activators from binding, hence altering their effects in a similar manner. In yet other embodiments, the peptides bind to c-Jun and induce a conformational change that inhibits phosphorylation or recruits co-repressors, thus altering c-Jun's function.

Western blotting results shows two in vitro modes of action upon treatment of TNBC cells with the CAPER peptides. The first occurs via decreased c-Jun activation, which is shown by the decrease in both c-Jun phosphorylation events. In certain embodiments, this decrease in c-Jun activity seen may result in decrease in AKT and subsequently phospho-AKT, since AKT can be controlled on the transcriptional level by the AP-1 heterodimer composed of c-Jun and b-Jun. AKT is a well-known pro-survival protein which exerts is activity through a variety of mechanisms, which include lower levels of FASL, phosphorylation of BAD, and the phosphorylation of Caspase 9, all of which are actions which have a pro-survival effect. Additionally markers for apoptosis, such as decrease in the level of pro-survival Bcl-2, shows the cells shifting to a pro-apoptotic state. c-Jun and NF-κB interact in a manner to suppress TNFα induced apoptosis. Indeed, the CAPER peptides increase phosphorylated NF-κB with a decrease in total NF-κB, both of which are seen during TNFα induced apoptosis. Therefore these results indicate that the CAPER peptides can increase TNFα induced apoptosis via impaired c-Jun function.

The CAPER peptides have shown no effect on cell cycle of TNBC cells in either the cell cycle assay or by changes in cyclin D1 levels. c-Jun affects cell cycle progression primarily through cyclin D1, though c-Jun's cell cycle and anti-apoptotic effects occur via different mechanisms and that the cell cycle effect does not require c-Jun phosphorylation to occur. Therefore in certain non-limiting embodiments the peptides can alter one aspect of c-Jun's function without effecting the other.

The second mode of action is related to CAPER's role in DNA repair. When TNBC cells are treated with CAPER peptides the same DNA repair proteins are decreased (RAD51 and c-abl) with an increase in a hallmark of DNA damage phospho-H2AX (γ-H2AX). In certain non-limiting embodiments, these proteins may form a complex with CAPER, and thus altering CAPER's activity and inhibiting these proteins from performing their vital role in DNA repair. In other non-limiting embodiments, this result is due to CAPER's alternate splicing function therefore causing the decrease in these proteins via alternative splicing defects.

These findings show that CAPER peptides are useful for the treatment of TNBC. In summary, the data presented here show for the first time the use of CAPER peptides as a mechanism for the treatment of patients with TNBC. Since this population is in a dire need of more treatment options, the work presented here paves the way for a targeted therapy for the treatment of this deadly disease.

ENUMERATED EMBODIMENTS

The following exemplary embodiments are provided, the numbering of which is not to be construed as designating levels of importance.

Embodiment 1 provides a method of treating cancer in a subject, the method comprising administering to the subject a therapeutically effective amount of a polypeptide consisting essentially of: (a) amino acid residues 356-400 of co-activator of activator protein-1 and estrogen receptor (CAPER) isoform HCC1.3 (corresponding to SEQ ID NO. 1) or (b) amino acid residues 356-400 of CAPER isoform HCC1.4 (corresponding to SEQ ID NO. 2).

Embodiment 2 provides the method of Embodiment 1, wherein the cancer comprises at least one of breast cancer, brain cancer, and lung cancer.

Embodiment 3 provides the method of Embodiment 2, wherein the breast cancer comprises triple negative breast cancer (TNBC) and/or estrogen-positive breast cancer.

Embodiment 4 provides the method of any of Embodiments 1-3, wherein the polypeptide is derivatized at at least one amino acid residue, wherein the derivatization comprises methylation, amidation, and/or acetylation.

Embodiment 5 provides the method of any of Embodiments 1-4, wherein the polypeptide is fused to a cell penetrating peptide.

Embodiment 6 provides the method of any of Embodiments 1-5, wherein the cell penetrating peptide is any of SEQ ID NOs. 10-47.

Embodiment 7 provides the method of any of Embodiments 5-6, wherein the polypeptide is fused to the cell penetrating peptide via a linker.

Embodiment 8 provides the method of Embodiment 7, wherein the linker comprises a polyethylene glycol (PEG) chain, a peptide, or a peptide nucleic acid (PNA).

Embodiment 9 provides the method of Embodiment 8, wherein the linker peptide comprises less than about 50 amino acids.

Embodiment 10 provides the method of any of Embodiments 1-9, wherein the polypeptide binds to the c-Jun component of activator protein-1 (AP-1) with an equilibrium dissociation constant (KD) ranging from about 5 nM to about 50 nM.

Embodiment 11 provides the method of Embodiment 10, wherein the binding of the polypeptide to the c-Jun component of activator protein-1 (AP-1) inhibits at least partially binding of the full-length CAPER protein to the c-Jun component of AP-1.

Embodiment 12 provides the method of any of Embodiments 1-9, wherein the polypeptide binds to the estrogen receptor (ER)α with an equilibrium dissociation constant (KD) ranging from about 5 nM to about 50 nM.

Embodiment 13 provides the method of Embodiment 12, wherein binding of the polypeptide to the ERα inhibits at least partially binding of the full-length CAPER protein to the ERα.

Embodiment 14 provides the method of any of Embodiments 1-13, wherein the administering induces DNA damage in cancer cells.

Embodiment 15 provides the method of any of Embodiments 1-14, wherein the administering causes apoptosis in cancer cells.

Embodiment 16 provides the method of any of Embodiments 1-15, wherein the administering does not cause any, or causes insignificant, apoptosis, and/or DNA damage in non-cancerous cells.

Embodiment 17 provides the method of any of Embodiments 1-16, wherein the polypeptide is administered as part of a pharmaceutical composition.

Embodiment 18 provides the method of any of Embodiments 1-17, wherein the subject is not administered any additional chemotherapeutic agent or anti-cell proliferation agent.

Embodiment 19 provides the method of any of Embodiments 1-17, wherein the subject is not administered any additional chemotherapeutic agent or anti-cell proliferation agent in an amount sufficient to treat or prevent the cancer in the subject.

Embodiment 20 provides the method of any of Embodiments 1-17, further comprising administering to the subject at least one additional agent selected from radiation, a chemotherapeutic agent, an anti-cell proliferation agent, a gene therapy agent, and an immunotherapy agent.

Embodiment 21 provides the method of Embodiment 20, wherein the polypeptide and the at least one additional agent are co-administered to the subject.

Embodiment 22 provides the method of any of Embodiments 20-21, wherein the polypeptide and the at least one additional agent are coformulated.

Embodiment 23 provides the method of any of Embodiments 20-22, wherein the at least one additional agent is selected from taxotere, cyclophosphamide, paclitaxel, fluorouracil, doxorubicin, cycloheximide, olaparib and temozolmide.

Embodiment 24 provides the method of any of Embodiments 1-23, wherein the subject is a mammal.

Embodiment 25 provides the method of Embodiment 24, wherein the subject is a human.

Embodiment 26 provides a polypeptide consisting essentially of: (a) amino acid residues 356-400 of co-activator of activator protein-1 and estrogen receptor (CAPER) isoform HCC1.3 (SEQ ID NO. 1) or (b) amino acid residues 356-400 of CAPER isoform HCC1.4 (SEQ ID NO. 2).

Embodiment 27 provides the polypeptide of Embodiment 26, wherein the polypeptide is (i) derivatized at at least one amino acid residue, wherein the derivatization comprises methylation, amidation, or acetylation; or (ii) fused to a cell penetrating peptide.

Embodiment 28 provides the polypeptide of Embodiment 27, wherein the cell penetrating peptide is any of SEQ ID NOs. 10-47.

Embodiment 29 provides the polypeptide of any of Embodiments 27-28, wherein the polypeptide is fused to the cell penetrating peptide via a linker comprising a polyethylene glycol (PEG) chain, a peptide, or a peptide nucleic acid (PNA).

Embodiment 30 provides the polypeptide of Embodiment 29, wherein the linker peptide comprises less than about 50 amino acids.

Embodiment 31 provides a pharmaceutical composition comprising the polypeptide of any of Embodiments 26-30.

Embodiment 32 provides a kit comprising the pharmaceutical composition of Embodiment 31 and an instructional material for use thereof, wherein the instructional material comprises instructions for treating cancer using the pharmaceutical composition.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating or ameliorating cancer in a subject, the method comprising administering to the subject a therapeutically effective amount of a polypeptide consisting essentially of:
   (a) amino acid residues 356-400 of co-activator of activator protein-1 and estrogen receptor (CAPER) isoform HCC1.3 (SEQ ID NO. 1);
   or
   (b) amino acid residues 356-400 of CAPER isoform HCC1.4 (SEQ ID NO. 2).

2. The method of claim 1, wherein the cancer comprises at least one of breast cancer, brain cancer, and lung cancer.

3. The method of claim 2, wherein the breast cancer comprises triple negative breast cancer (TNBC) or estrogen-positive breast cancer.

4. The method of claim 1, wherein the polypeptide is derivatized at at least one amino acid residue, wherein the derivatization comprises methylation, amidation, or acetylation.

5. The method of claim 1, wherein the polypeptide is fused to a cell penetrating peptide, optionally wherein the cell penetrating peptide is any of SEQ ID NOs. 10-47.

6. The method of claim 5, wherein the polypeptide is fused to the cell penetrating peptide via a linker, optionally wherein the linker comprises a polyethylene glycol PEG) chain, a peptide, or a peptide nucleic acid (PNA), wherein the optional linker peptide optionally comprises less than about 50 amino acids.

7. The method of claim 1, wherein the polypeptide binds to at least one of the following:
   (a) the c-Jun component of activator protein-1 (AP-1) with an equilibrium dissociation constant ($K_D$) ranging from about 5_nM to about 50_nM, optionally wherein binding of the polypeptide to the c-Jun component of the activator protein-1 (AP-1) inhibits, at least partially, binding of the full-length CAPER protein to the c-Jun component of AP-1; and
   (b) the estrogen receptor (ER)α with an equilibrium dissociation constant ($K_D$) ranging from about 5 nM to about 50 nM, optionally wherein binding of the polypeptide to the ERα inhibits, at least partially, binding of the full-length CAPER protein to the ERα.

8. The method of claim 1, wherein the administering induces DNA damage or apoptosis in cancer cells, optionally wherein the administering does not cause any damage, or causes insignificant, apoptosis, or DNA damage in non-cancerous cells.

9. The method of claim 1, wherein the polypeptide is administered as part of a pharmaceutical composition.

10. The method of claim 1, wherein the subject is not administered any additional chemotherapeutic agent or anti-cell proliferation agent.

11. The method of claim 1, further comprising administering to the subject at least one additional agent selected from radiation, a chemotherapeutic agent, an anti-cell proliferation agent, a gene therapy agent, and an immunotherapy agent.

12. The method of claim 11, wherein the polypeptide and the at least one additional agent are co-administered to the subject, optionally wherein the polypeptide and the at least one additional agent are coformulated.

13. The method of claim 11, wherein the at least one additional agent is selected from taxotere, cyclophosphamide, paclitaxel, fluorouracil, doxorubicin, cycloheximide, olaparib and temozolomide.

14. The method of claim 1, wherein the subject is a mammal, which is optionally human.

* * * * *

UNITED STATES PATENT AND TRADEMARK OFFICE
CERTIFICATE OF CORRECTION

| | |
|---|---|
| PATENT NO. | : 12,201,671 B2 |
| APPLICATION NO. | : 17/607100 |
| DATED | : January 21, 2025 |
| INVENTOR(S) | : Jean-Francois Jasmin, Shannon Chilewski and Isabelle Mercier |

It is certified that error appears in the above-identified patent and that said Letters Patent is hereby corrected as shown below:

In the Claims

Column 55, Claim 6, Line 26, please replace "polyethylene glycol PEG)" with -- polyethylene glycol (PEG) --

Column 55, Claim 7, Line 34, please replace "from about 5_nM to about 50_nM," with -- from about 5 nM to about 50 nM, --

Signed and Sealed this
Thirteenth Day of May, 2025

Coke Morgan Stewart
*Acting Director of the United States Patent and Trademark Office*